US009466088B2

(12) United States Patent
Perazzo et al.

(10) Patent No.: US 9,466,088 B2
(45) Date of Patent: Oct. 11, 2016

(54) AUTOMATED ORAL SYRINGE PACKAGING SYSTEM FOR HOSPITAL PHARMACIES

(71) Applicants: Nicholas J Perazzo, Rosedale, MD (US); Robert A Rosen, Owings Mills, MD (US); John G Grosskopf, Jr., Ellicott City, MD (US); Mark Bennett, Ellicott City, MD (US); John M Chopper, Pasadena, MD (US)

(72) Inventors: Nicholas J Perazzo, Rosedale, MD (US); Robert A Rosen, Owings Mills, MD (US); John G Grosskopf, Jr., Ellicott City, MD (US); Mark Bennett, Ellicott City, MD (US); John M Chopper, Pasadena, MD (US)

(73) Assignee: National Instrument, LLC, Baltimore, MD (US)

( * ) Notice: Subject to any disclaimer, the term of this patent is extended or adjusted under 35 U.S.C. 154(b) by 468 days.

(21) Appl. No.: 13/788,849

(22) Filed: Mar. 7, 2013

(65) Prior Publication Data

US 2014/0157731 A1  Jun. 12, 2014

Related U.S. Application Data

(63) Continuation-in-part of application No. 13/236,577, filed on Sep. 19, 2011, now Pat. No. 9,033,006.

(60) Provisional application No. 61/607,867, filed on Mar. 7, 2012.

(51) Int. Cl.
| | | |
|---|---|---|
| *B65B 3/00* | (2006.01) | |
| *G06Q 50/22* | (2012.01) | |
| *B65B 5/04* | (2006.01) | |
| *G01N 21/84* | (2006.01) | |
| *G06Q 10/08* | (2012.01) | |
| *B65B 57/02* | (2006.01) | |
| *B65B 3/28* | (2006.01) | |
| *B65B 3/30* | (2006.01) | |
| *B65B 7/28* | (2006.01) | |
| *G06F 19/00* | (2011.01) | |
| *A61J 7/00* | (2006.01) | |

(52) U.S. Cl.
CPC ............... *G06Q 50/22* (2013.01); *B65B 3/003* (2013.01); *B65B 3/28* (2013.01); *B65B 3/30* (2013.01); *B65B 5/045* (2013.01); *B65B 7/28* (2013.01); *B65B 57/02* (2013.01); *G01N 21/84* (2013.01); *G06F 19/3456* (2013.01); *G06F 19/3462* (2013.01); *G06Q 10/087* (2013.01); *A61J 7/0053* (2013.01)

(58) Field of Classification Search
CPC ......... B65B 3/003; B65B 59/00; B65B 1/20; A61J 1/20; A61J 1/2096
USPC ............ 141/27, 152, 98, 329; 700/231, 232, 700/239
See application file for complete search history.

(56) References Cited

U.S. PATENT DOCUMENTS

| | | |
|---|---|---|
| 4,493,348 A | 1/1985 | Lemmons |
| 5,692,640 A | 12/1997 | Caulfield |
| 5,884,457 A | 3/1999 | Ortiz |
| 6,877,530 B2 * | 4/2005 | Osborne ............... B65B 7/2821 141/198 |

(Continued)

*Primary Examiner* — Mark A Laurenzi
*Assistant Examiner* — Timothy P Kelly
(74) *Attorney, Agent, or Firm* — Ober, Kaler, Grimes & Shriver

(57) ABSTRACT

A fully-automated system suitable for use in a hospital setting for filling patient-specific liquid prescriptions to be administered by oral syringes on a just-in-time basis. The system enables hospital pharmacists to simplify and streamline their task, increasing the number of prescriptions that can be filled in a day, improving patient safety and care by minimizing medication errors and the consequences that ensue.

35 Claims, 25 Drawing Sheets

(56) References Cited

U.S. PATENT DOCUMENTS

| | | |
|---|---|---|
| 6,976,349 B2 | 12/2005 | Baldwin |
| 6,991,002 B2 | 1/2006 | Osborne |
| 7,017,622 B2 | 3/2006 | Osborne |
| 7,117,902 B2 | 10/2006 | Osborne |
| 7,240,699 B2 | 7/2007 | Osborne |
| 7,260,447 B2 | 8/2007 | Osborne |
| 7,343,943 B2 | 3/2008 | Khan |
| 7,610,115 B2 | 10/2009 | Rob |
| 7,631,475 B2 | 12/2009 | Baldwin |
| 7,681,606 B2 | 3/2010 | Khan |
| 2004/0154690 A1* | 8/2004 | Osborne ............ B01F 13/1072 141/27 |
| 2008/0035234 A1* | 2/2008 | Khan .................... B65B 3/003 141/27 |
| 2009/0067973 A1 | 3/2009 | Eliuk |
| 2010/0017031 A1 | 1/2010 | Rob |

\* cited by examiner

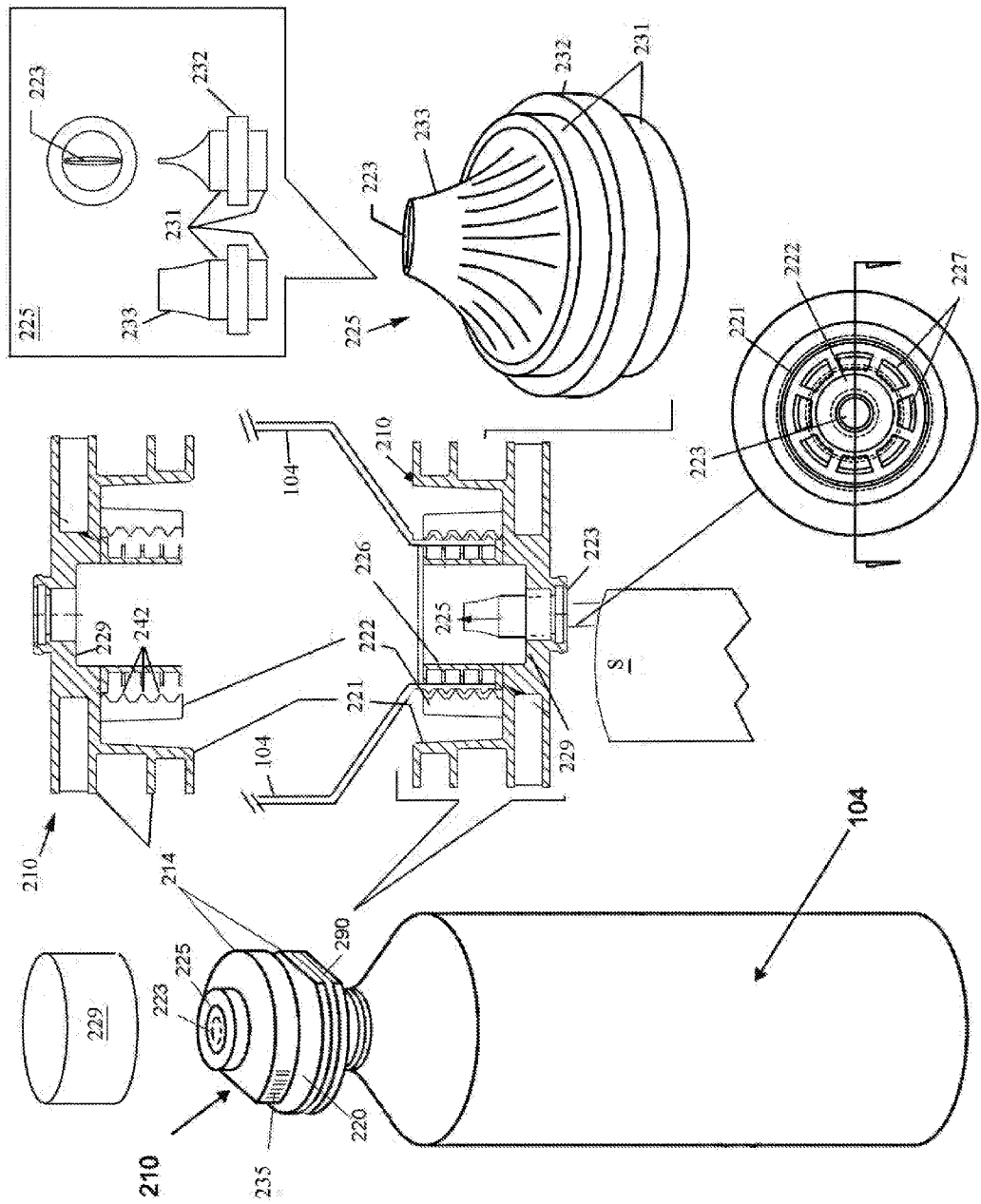

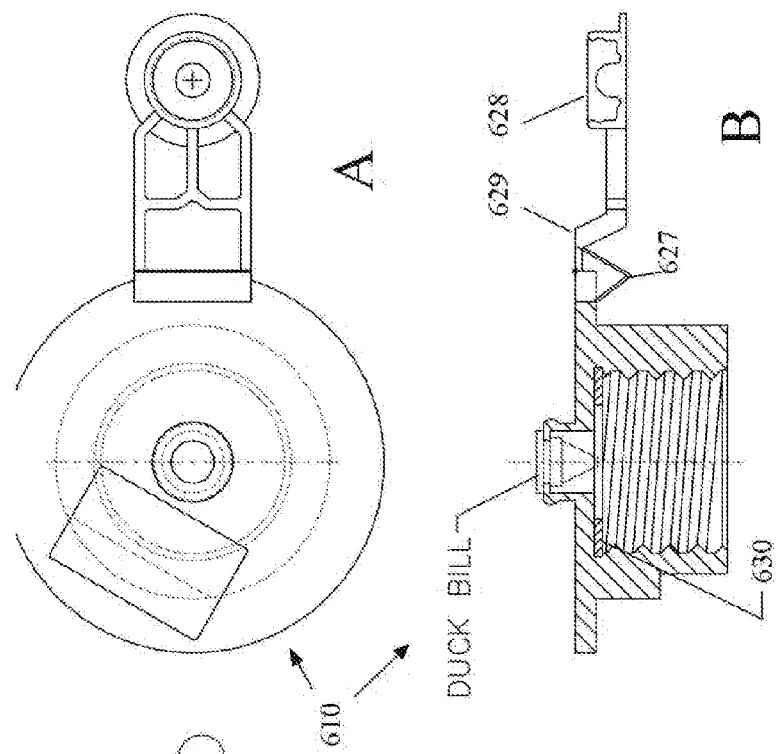
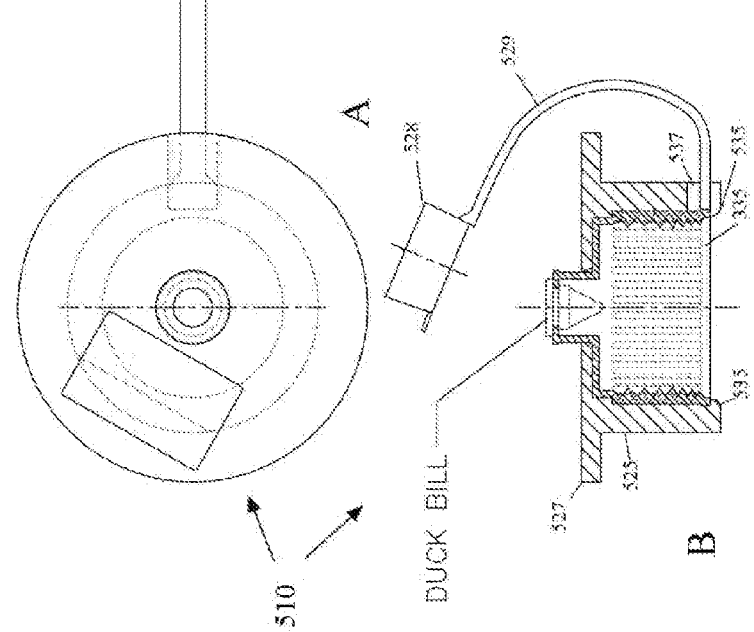

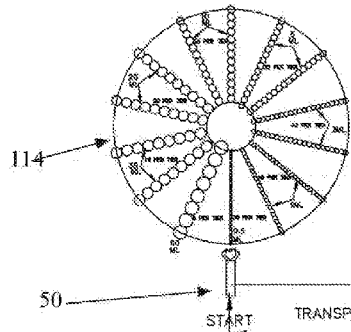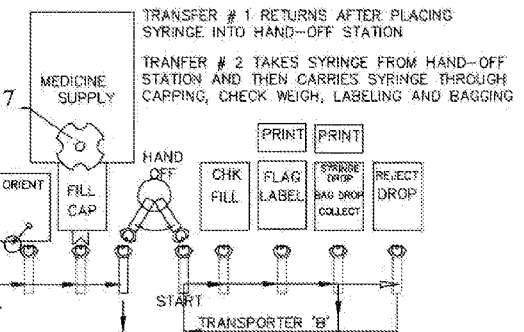
FIG. 18
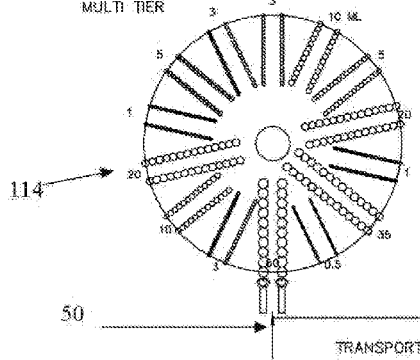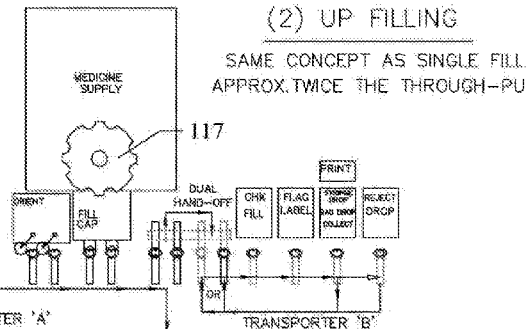
FIG. 19

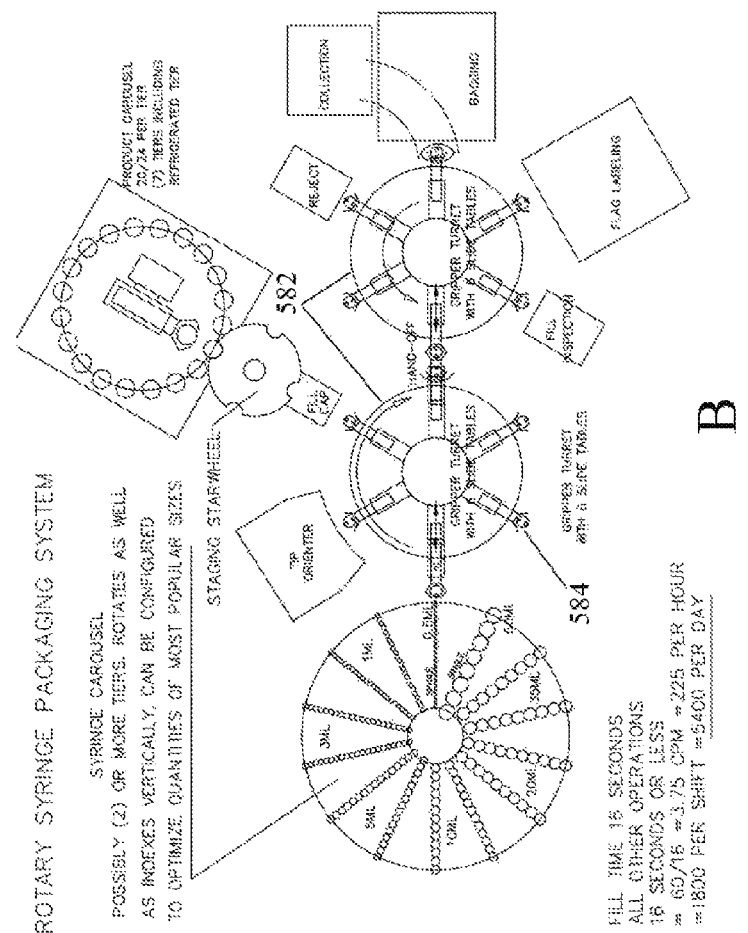
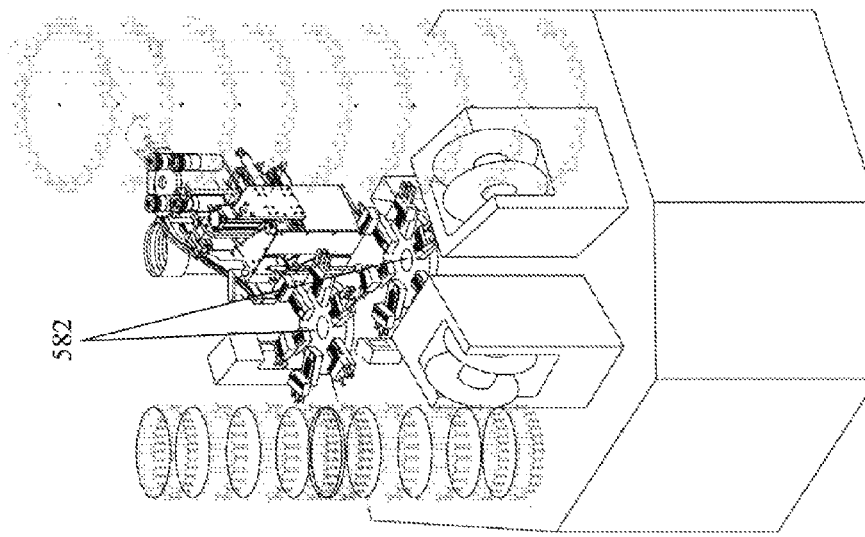
FIG. 21

AUTOMATED ORAL SYRINGE PACKAGING SYSTEM FOR HOSPITAL PHARMACIES

CROSS-REFERENCE TO RELATED APPLICATIONS

The present application claims priority to U.S. provisional patent application Ser. No. 61/607,867 filed 7 Mar. 2012, and is a continuation-in-part of U.S. patent application Ser. No. 13/236,577 filed 19 Sep. 2011 (which claims priority to U.S. provisional patent application Ser. No. 61/384,217 filed Sep. 17, 2010 and to U.S. provisional patent application Ser. No. 61/494,677 filed Jun. 8, 2011, both of which are incorporated herein by reference).

BACKGROUND OF THE INVENTION

1. Field of the Invention

The present invention relates generally to oral syringe packaging equipment and more specifically to a fully automated system for preparing patient-specific doses of selected pharmaceutical liquid medication for administration by oral syringe on a patient specific, just-in-time, medication error-free, and cost effective basis, for use in a hospital pharmacy.

2. Description of the Background

Oral syringes are well known instruments in the medical fields and are used to administer liquid medicine into the mouth, typically for infants/children and uncooperative or geriatric adults, as an alternative to pills which can present a choking hazard or be expectorated. The oral syringe directs liquid medicine to the back of the throat prompting a swallowing response. Injectable syringes, on the other hand, are used to administer medication into the body by injecting its contents through the skin. Injectable syringes utilize a needle on the tip of the syringe. Injectable syringes must be manufactured and packaged in a sterile environment. Research has shown that the potential for adverse drug events within the pediatric inpatient population is about three times as high as among hospitalized adults. See, Joint Commission, Preventing Pediatric Medication Errors, Issue 39 (2008). According to the Commission Report, the most common types of harmful pediatric medication errors were improper dose/quantity (37.5 percent) and unauthorized/wrong drug (13.7 percent), followed by improper preparation or dosage form. Oral syringes help to minimize these problems and are considered the gold standard for delivering medicine to children.

Oral syringes comprise a simple piston pump with a plunger that fits tightly in one end of a cylindrical tube (the barrel) and can be pushed or pulled along inside the barrel to create negative or positive relative pressure within the barrel that causes the syringe to take in or expel a liquid or gas through an orifice at the opposing end of the barrel. The barrel of an oral syringe is typically made of plastic and is at least partially transparent along its length with graduated markings to indicate the volume of fluid in the syringe based on the position of the plunger. Oral syringes come in a wide range of sizes, some with nozzle located centrally and some offset from center, and this variability makes it difficult to automate the filing process. Oral syringes are commonly marked in units of milliliters and come in standard sizes ranging from 0.5 to 60 milliliters. An annular flange partially or fully encircling the outside surface of the barrel is typically provided to facilitate compression of the plunger into the barrel. The plunger is also typically plastic as this provides a good seal within the barrel and is inexpensive to produce so as to be disposable, reducing the risk of contamination or transmission of spreading disease.

Pharmacies at in-patient medical facilities and other medical institutions fill a large number of prescriptions on a daily basis including prescriptions for liquid or compounded suspension medicines to be administered by oral syringe and must do so accurately for medical safety reasons. The volume of an oral pediatric prescription's dose is determined by the child's weight. This makes it impractical to stock pre-filled syringes due to the wide range of fill volumes required. As a result, pediatric oral liquid doses are prepared in the hospital pharmacy on a patient-specific, just-in-time basis. The process of filling numerous, variously sized single dose prescriptions for delivery by oral syringe is time consuming, labor intensive and prone to human error. Moreover, the manual manipulation of all the myriad prescription bottles as well as variously-sized oral syringes can lead to injury such as carpal tunnel syndrome. To insure that the medication is packaged error-free, the pharmacy technician must make sure that: (1) the syringe contains the correct medication; (2) the syringe contains the correct amount of medication: (3) the syringe is capped correctly; (4) the medication has not expired; (5) the medication has not been recalled; (6) the medication, when required, is shaken; (7) the medication, when required, has been properly refrigerated; (8) the medication, when required, has been properly protected from exposure to light; (9) the information on the syringe label is correct: (10) the syringe is placed into the correct bag; (11) the information on the bag containing the syringe is correct; (12) the bag is properly sealed; and (13) the syringe is protected from cross contamination from other medications. The process typically requires a pharmacist or pharmacy technician to retrieve the correct medication from a storage cabinet or refrigerated storage area. The liquid medications are typically stored in a container sealed with a safety cap or seal. After confirming the contents of the retrieved container and shaking the medication (if necessary), the technician opens the cap and inserts the tip of an oral syringe into the container, withdrawing the plunger to draw the medication into the barrel of the syringe. After filling with a proper amount, the tip of the syringe is covered with a cap for transport to the patient, and the syringe is labeled to indicate its content, the intended recipient, and then bagged. Prior to administering the dose, the nurse use determine the amount of the dose by observing where the tip of the plunger or piston is located in the barrel. Most oral syringes are marked for measuring the dose in milliliters (mL). Oral syringes are relatively inexpensive and disposable.

Currently, the degree of automation in the hospital pharmacy for the packaging of oral syringes is very limited. Islands of automation exist, such as automatic labeling of the syringe and bagging of the filled and capped syringe. However, the filling and capping are done manually. Scanners, cameras, bar code readers and track and trace technology have not been applied on an integrated, comprehensive basis for the packaging of oral syringes in the hospital pharmacy. The potential to reduce medication errors using this technology is significant. Automated systems have been developed by Baxa, Inc., For Health Technologies, Inc., Intelligent Hospital Systems and others for the automated filling of injectable syringes.

For example, U.S. Pat. Nos. 6,991,002, 7,017,622, 7,631,475 and 6,976,349 are all drawn to automated removal of a tip cap from an empty syringe, placing the tip cap at a remote location, and replacing the tip cap on a filled syringe. U.S. Pat. Nos. 7,117,902 and 7,240,699 are drawn to automated transfer of a drug vial from storage to a fill station. U.S. Pat. No. 5,884,457 shows a method and apparatus for filling injectable syringes using a pump connected by hose to a fluid source. U.S. Pat. No. 7,610,115 and Application 20100017031 show an Automated Pharmacy Admixture System (APAS). US Application 20090067973 shows a gripper device for handling syringes with tapered or angled gripper fingers. U.S. Pat. No. 7,343,943 shows a medication dose underfill detection system. U.S. Pat. No. 7,260,447 shows an automated system for fulfilling pharmaceutical prescriptions. U.S. Pat. No. 7,681,606 shows an automated system and process for filling injectable syringes of multiple sizes. U.S. Pat. No. 6,877,530 shows an automated means for withdrawing a syringe plunger. U.S. Pat. No. 5,692,640 shows a system for establishing and maintaining the identity of medication in a vial using preprinted, pressure sensitive, syringe labels.

The foregoing references are generally suitable for packaging injectable syringes. The packaging process required for injectable syringes is significantly different than that for oral syringes. Injectable syringes must be packaged in a sterile environment as the medication is injected into the body. This requirement adds cost and complexity to the machine. Injectable medications when packaged on a just-in-time basis, as with the Baxa, For Health Technologies, and Intelligent Hospital System machines, must typically be prepared by the machine before the medication is filled into the syringe. The medication preparation process involves diluting the medication or reconstituting the medication from a powder with water. This process adds expense and slows down the packaging process as well. The Intelligent Hospital Systems syringe packaging system is designed to be used to package cytotoxic medications which are hazardous. To avoid harm to the operator, this machine uses a robot located within an isolator barrier at considerable cost. The Baxa, For Health Technologies, and Intelligent Hospital System machines require the use of expensive disposable product contact parts when a different medication is to be filled. The foregoing machines are not suitable for packaging oral syringes due to their capital cost, complexity, slow production rates, inability to handle oral medication containers, and the requirement of expensive disposable contact parts. Consequently, existing automation does not address the needs of medical institutions desiring an affordable pharmacy automation system for patient safety, prescription tracking and improved productivity. The present invention was developed to fill this void.

Oral syringes are manufactured in a variety of sizes with differing tip and plunger configurations. Moreover, oral medications are commonly provided in bulk form in variously-sized bottles or containers having threaded screw caps that must be removed and replaced between uses. For example, U.S. Pat. No. 4,493,348 shows a method and apparatus in which oral syringes can be filled using a screw-on adapter cap 12 for connecting the bulk medicine container 10 and a syringe 14 so that the liquid medication can be transferred from the bulk container 10 into the syringe barrel 20. The syringe is inserted into a nozzle 88 of the adapter cap 12 and displaces a detent valve 92 (see FIG. 6) that allows medicine to flow through the nozzle 88 into the syringe. When not in use the nozzle 88 may be closed off by a plug 50 attached to a tether 48. The adapter cap 12 is well-suited for manual filling of oral syringes but is not suitable for automated filling. The design of the cap 12 is specific to only one size of bulk medicine container and one size syringe nozzle. The variety of bulk container sizes and syringe sizes with differing tip and plunger configurations would require a large inventory of adapter caps 12 in an automated environment. Given the diversity of oral syringes and medicine containers available, any fully automated system will need sufficient dexterity to manipulate all the myriad prescription bottles containing the pharmaceuticals to be dispensed as well as variously-sized oral syringes, bringing them together in a controlled environment to quickly and accurately fill and label each syringe and to verify its work as it proceeds in order to avoid errors in the process. Such a system would need to be reliably constructed so as to minimize downtime, quickly take and fill orders, be easy to clean and capable of maintaining an environment free from cross contamination. Such a system would also need to be able to interact with a human operator throughout the operation.

Additionally, in-patient medical facilities such as hospitals are moving toward electronic prescription (e-prescription) systems which use computer systems to create, modify, review, and/or transmit medication prescriptions from the healthcare provider to the pharmacy. While e-prescribing improves patient safety and saves money by eliminating the inefficiencies and inaccuracies of the manual, handwritten prescription process, any syringe fill automation system suitable for use in a hospital setting must interface with an existing e-prescription system (which records and transmits prescriptions to the pharmacy), and must be capable of filling prescription orders in a just-in-time environment.

The present inventors herein provide a fully-automated system suitable for use in a hospital setting for filling patient-specific doses of liquid medications to be administered by oral syringes on a patient specific, just-in-time, medication error-free, and cost effective basis. The system enables hospital pharmacists to simplify and streamline their task, increasing the number of prescriptions that can be filled in a day while avoiding the risk of human error and the risk of carpal tunnel syndrome to the pharmacist or technician, improving both patient and pharmacist/technician safety and care. Direct supervision of the technician by the pharmacist is reduced due to the inspection/track and trace system that minimizes the opportunity for error.

BRIEF DESCRIPTION OF THE DRAWINGS

The objects, features, and advantages of the present invention will become apparent from the following detailed description of the preferred embodiments and certain modifications thereof when taken together with the accompanying drawings in which like numbers represent like items throughout and in which:

FIG. 5 is a composite view of an adapter cap 210 according to an embodiment of the present invention.

FIG. 6A is a top view and FIG. 6B a section view of an alternate embodiment of the adapter cap 510 adapted for retrofit assembly to an existing medicine container cap, with a tethered overcap 528.

FIG. 7A is a top view and FIG. 7B a section view of another alternate embodiment of an adapter cap 610 adapted for retrofit assembly to an existing medicine container cap and in which a spout cap 628 is molded to overcap 625 by a resilient arm 629 that is attached at a plastic hinge.

FIG. 8A is a perspective view of an exemplary syringe nozzle tip orientation station 8 while FIGS. 8B and 8C are detailed front and side views, respectively, of the orientation station 8.

FIG. 18 is a drawing of the sectionalized syringe conveyor 50 for shuttling along the Automated Filling/Packaging Station 4.

FIG. 19 illustrates how the rotating multi-tiered servomotor-driven carousel 3 syringe storage of FIG. 17 and conveyor 50 can be doubled-up to increase throughput.

FIG. 21A is a perspective view and 21B a top view of another alternate embodiment in which the linear syringe conveyor 50 is replaced by a pair of side-by-side gripper turrets 582.

DETAILED DESCRIPTION OF THE PREFERRED EMBODIMENT

Figure 1:
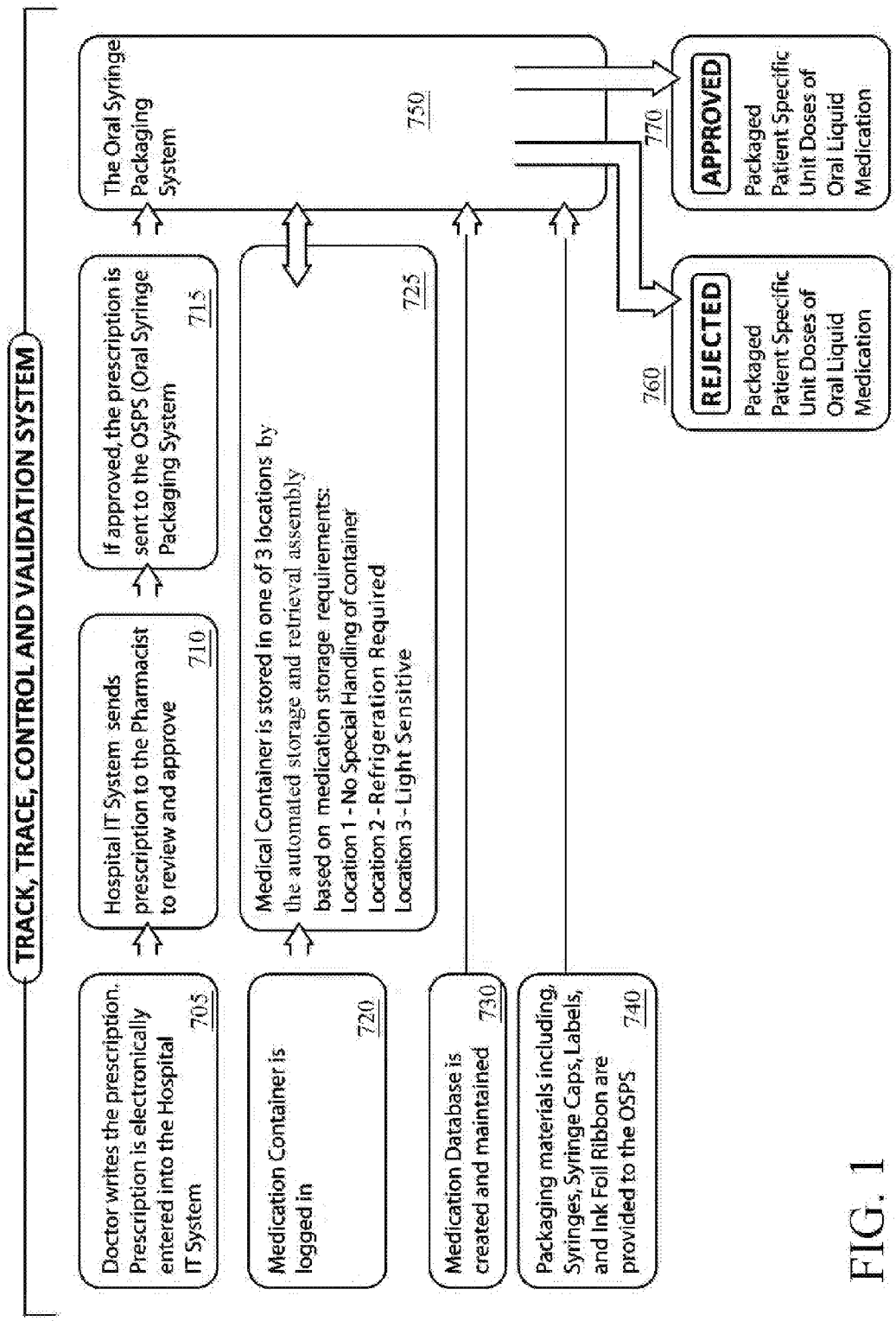
FIG. 1 is a flow chart of the overall method of the invention.

For the purposes of promoting an understanding of the principles of the invention, reference will now be made to the exemplary embodiment illustrated in the drawings and described below. The embodiment disclosed is not intended to be exhaustive or limit the invention to the precise form disclosed in the following detailed description. Rather, the embodiment is chosen and described so that others skilled in the art may utilize its teachings. It will be understood that no limitation of the scope of the invention is thereby intended. The invention includes any alterations and modifications in the illustrated device, the methods of operation, and further applications of the principles of the invention which would normally occur to one skilled in the art to which the invention relates.

The present invention includes both the system hardware as well as the process for preparing and tracking prescriptions of oral syringes by a series of integrated automated steps with respect to preparing the syringe and the bulk medicine, and subsequently bringing the series together for filling the former from the latter. The invention relies on a conventional network architecture which includes a local oral syringe packaging system (OSPS) computer. The OSPS computer is interfaced to a hospital host computer and receives oral syringe prescription instructions there from. In the majority of circumstances, physicians submit prescriptions for oral syringes electronically to the hospital host computer, and these are communicated to the OSPS computer for fulfillment. A software interface resident on the OSPS computer serves to parse/extract those oral medication prescriptions from all prescriptions submitted.

The local OSPS computer is programmed to know what must occur at each station and monitor it to ensure that each step of the process is completed satisfactorily and that all decision rules are complied with. Generally, the local OSPS computer software implements a Medication Container Orientation and Log-In Process for semi-automated preparation and storage of the bulk medicine containers to be used in filling and packaging oral syringes, and a Batch Fulfillment Process for fully-automated filling and packaging of oral syringes using the stored bulk medicine containers. The Medication Container Orientation and Log-In Process is independent of the Batch Fulfillment Process, and in general terms comprises the following steps:

a. Bulk medication containers received from the pharmaceutical manufacturer are delivered to a Medication Container Orientation and Log-In Station where an operator (i.e. a Pharmacy Technician and/or a Pharmacist) logs into the OSPS computer;

b. Each medication container label is photographed using a label photographing station resident at the Medication Container Orientation and Log-In Station. This retains a permanent digital record of the medication used to fill a specific prescription, and where a barcode scan (see next step) is insufficient to identify the concentration, expiration, handling and/or other precautions to be taken relative to this medication, subsequent reference to the recorded label photograph provide the missing information. Each medication container barcode is scanned using a scanner resident at the Medication Container Orientation And Log-In Station and Product Information gained from the scan is automatically entered into the OSPS computer. The operator is provided with a manual data entry screen for entry of any missing or variable information such as container fill size, manufacturer's expiration date, product lot number. The OSPS computer hosts a database and creates a record for each logged bulk medication container, inclusive of Product Information and label photograph, and each record is automatically tagged with the time and date that the medication container orientation takes place. The record includes a medicine storage designation such as container capacity, expiration date, lot number, time and date of container log-in, and "Standard", "Refrigerated", or "Light Sensitive" to ensure proper storage.

c. The OSPS local computer instructs the operator which of a variety of adapter caps (described below) to select for recapping the medication container. The medicine container caps are not uniform, and a uniform adapter cap facilitates downstream automation. The operator manually removes the manufacturer's cap from the bulk medicine containers using an optional capper/decapper device (described below) resident at the Medication Container Orientation And Log-In Station, and replaces that cap with a designated adapter cap. The adapter cap selection is visually guided (e.g., the box containing the correct size adapter cap will light) by the OSPS computer.

d. The OSPS computer generates a 2D barcode label which includes the location where the medication container is to be stored and the type of storage (Standard, Refrigerated, and Light Sensitive) in which the container is to be placed. The label is printed on a printer at the Medication Container Orientation And Log-In Station, and is applied by the operator preferably to the adapter cap (but alternatively elsewhere such as the bottom of the medicine container.

e. The operator rescans the manufacturer's barcode on the medication container and the adapter cap 2D barcode. The OSPS computer assigns and records a storage location for the container in a medication Storage Facility (to be described). The OSPS computer also assigns and records an effective expiration date for the medication container (the "effective expiration date" is determined by the date the container is opened at the Medication Container Log In Station plus a predetermined number of days based on pharmacy policy that the medication should expire, not in excess of the manufacturer's expiration date).

f. The container is automatically stored in the assigned location of the Medication Storage Facility by an automated storage and retrieval assembly. If the container is to be stored in the refrigerated section of the Storage Facility, or in light protected storage, a log-in/log-out control system verifies that the container was refrigerated and/or light-protected satisfactorily.

It should be understood that the medication container may be provided by the pharmaceutical packager with the information required to utilize that container in the OSPS System 100 on a 2D bar code preferably applied to the center of the base of the container, or with means such as an RFID tag. Doing so would avoid the data collection procedure described previously. However, an adapter cap would still be required to replace the original cap unless the pharmaceutical packager provided the medication with the adapter cap already installed. If the medication container cap needed to be replaced with an adapter cap, the pharmacist/technician could scan the 2D bar code applied to the center of the base of the container, and generate an identical 2D bar code label that would be placed on the adapter cap.

The Automated Fulfillment Process comprises the following steps:

a. The operator selects from among the operating modes of the system (to be described) and submits an oral syringe fulfillment order which may comprise one or more oral syringe prescriptions to be fulfilled. The OSPS computer analyzes the fulfillment order and orchestrates automated filling and packaging of the oral syringes using the stored bulk medicine containers as follows.

b. The OSPS computer identifies the appropriate medication container from the particular (logged) Storage Facility location and makes sure that all medication issues relating to that medicine container have been addressed, including refrigeration, expiration and light-sensitive storage.

c. The OSPS computer retrieves the selected medication container from the particular (logged) Storage Facility location.

d. The OSPS computer automatically loads the selected medicine container into a product interface at the fill/cap station.

e. The OSPS computer automatically picks a syringe based on a fill-size calculation that calculates the most appropriate standard syringe size increment from the requested prescription volume.

f. The system automatically inspects the syringe for proper size, based on a syringe body measurement (described below), to verify that the correct syringe has been selected.

g. If syringe size is correct, the system transports and loads the syringe into the fill/cap station.

h. System/software automatically fills the syringe from medicine in medication container and caps the syringe.

i. The system scans the syringe at a volume/weight check station.

j. If syringe volume/weight is correct, the OSPS computer automatically prints and inspects a label for the syringe and the pre-printed label is attached to the syringe.

k. The system automatically prints a bag that the syringe will be packaged in, and automatically scans the printing on the bag to make sure that it is correct l. The system automatically places the syringe in the bag, confirms that the syringe was placed in the bag, and seals the bag with the syringe in it.

All medication containers and medicines in those containers that have been logged in, each size syringe, each size adapter cap, syringe labels, bags, ink cartridges, etc. are automatically inventoried. As an item is used or consumed, the amount of that item remaining is maintained. Track, Trace, and Validation software monitors and documents the entire process from the prescription approval by the pharmacist, the log-in of the medication container, and each step of the packaging process.

FIG. 1 is a more detailed flow chart of the overall method of the invention. The following method steps are performed automatically with software guided interaction with an operator, for filling patient-specific oral syringes on a just-in-time basis. The present method and apparatus is specifically designed to avoid mistakes and maintains comprehensive track-and-trace validation of each step:

At step 705 a physician writes an oral medicine prescription which is electronically entered into the existing hospital host computer (as all prescriptions are so logged).

At step 710 the existing hospital host computer communicates the oral medicine prescription to the hospital pharmacy computer for approval. A pharmacist will typically review it.

If approved, then at step 715, the prescription is transmitted to the local computer of the OSPS (Oral Syringe Packaging System) of the present invention. The operator may select from a variety of OSPS operational modes as will be described. The most typical of which is Patient Specific—Hospital Directed Mode. The oral syringe prescription is added to a batch fulfillment queue at the local OSPS computer. As described below the queue is multi-sorted so that all prescriptions for a particular type of medicine (e.g., Acetaminophen, cough syrup, etc.) can be fulfilled together, and at periods throughout the day an operator may run a batch fulfillment queue (typically batches are run a few times each day).

At commencement of batch fulfillment, the OSPS system automatically retrieves the appropriate medication container from OSPS storage facility (as will be described). This presupposes that a library of medicine containers is maintained and that each such medicine container has been properly logged and oriented into the OSPS system so that its location and contents are known to the local OSPS computer. Consequently, the above-described Orientation and Log-In Process is a precursor to batch fulfillment, where each new medication container is logged into OSPS storage by a barcode, RFID scan or similar identification scan (e.g., of the manufacturer's barcode). The manufacturer-applied cap must also be replaced by an adapter cap (to be described). Orientation and Log-In occurs at step 720.

At step 725 based on the medication container login, the operator places the medicine container in an automated storage and retrieval assembly and the OSPS system automatically conveys it to a Storage Facility, placing it in storage at a particular location specified by the OSPS local computer.

The OSPS system (as described below) includes separate storage locations for three types of medication containers: Location 1—No Special Handling of container; Location 2-Refrigeration required; Location 3—Light Sensitive medication container. The end result is an OSPS Storage Facility of different oral medicines in their bulk containers, each properly logged in and stored in its corresponding storage location 1-3. The location that the medication container is to be stored at is assigned by the OSPS computer with reference to a medication inventory management database. That location is printed on the medication 2D bar code label attached either to the adapter cap or to the base of the container.

Similarly, at step 740, an inventory of packaging materials is maintained, including empty syringes in an array of sizes, syringe caps, labels (for barcodes), printer ribbon, and bags.

In support of the OSPS system, at step 730 a comprehensive medication database is maintained at the OSPS computer.

The OSPS medication database generally includes 1) product information from the manufacturer or other external sources describing the medicines and their containers (size, dose, handling requirements, etc.); 2) prescription-specific information from the hospital identifying the prescription details and patient to receive it; and 3) OSPS runtime information such as the amount of medicine previously taken from a given bulk container. Specific items of information include the following:

1. Product Information.
   a. Medication name.
   b. Manufacturers barcode number.
   c. Written information that corresponds to manufacturer's barcode number.
   d. Whether medication needs to be shaken, if so the frequency and duration between fills.
   e. Whether the medication needs to be refrigerated, if so refrigeration policy required.
   f. Whether the medication is light sensitive, if so light sensitive protection.
   g. Manufacturer's Expiration Date.
   h. Fill size of that container in cc's.
2. Prescription-specific information
   a. Pharmacy Policy Expiration Date: Container open date plus the number of days before the container expires (determined by pharmacist).
   b. Effective Expiration Date. This is the soonest of the manufacturer's expiration date or the date that the container is open plus the number of days before the open container expires (Pharmacy Policy Expiration Date).
3. OSPS runtime information (pertaining to the individualized medication containers logged in).
   a. The OSPS 2D barcode number assigned to that specific container.
   b. Current amount of product remaining in that container after deducting for previous fills extracted by the syringes.
   c. Date the medication container is logged-in at the Medication Container Log-In Orientation System.

Given all of the foregoing, at step 750 an operator may at any convenient time commence the batch fulfillment process.

After each oral syringe has been filled and packaged during batch fulfillment 750, it is inspected and either rejected at step 760 or approved at step 770.

The above-described method is herein implemented in several detailed embodiments of a system suitable for preparing patient-specific oral syringe doses. Various alternate embodiments of the invention may omit selected steps (and their performance station) where such is/are not required. The needs of the operating institution and the cost aspect of automating certain steps may direct that certain steps/stations be performed manually (e.g. syringe selection and loading into the transport device, medication container storage/retrieval) by an operator interfacing with the apparatus. A presently-preferred fully-automated embodiment is described below with reference to FIG. 2.

Figure 2:
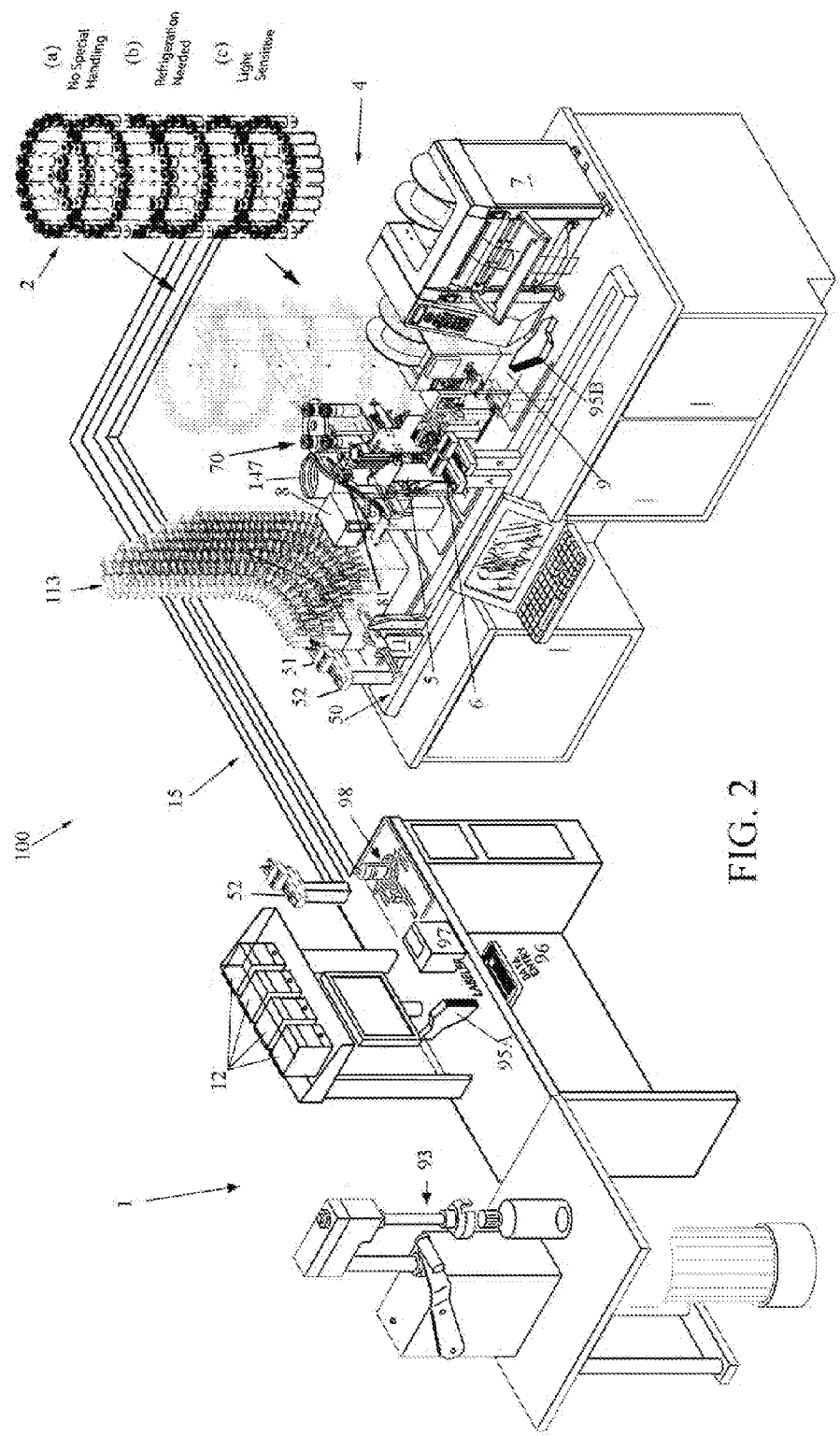
FIG. 2 is a perspective view of the entire pharmacy automation system 100 according to an embodiment of the invention.

As seen in FIG. 2, the pharmacy automation system 100 for packaging oral syringes generally comprises a stand-alone Medication Container Login & Orientation Station 1, with an included array of adapter cap storage bins 12. Logged/Oriented Medication Containers are transported from Station 1 along an automated storage and retrieval assembly 15 to a Storage Facility 2 in which all logged medication containers are stored. Storage facility 2 has separate locations for the three types of medication containers: (a) Location 1—No special handling of container; (b) Location 2—Refrigeration required; and (c) Location 3—Light Sensitive medication container.

Storage Facility 2 is proximate an Automated Filling and Packaging Station 4. The Automated Filling/Packaging Station 4 includes a storage bin 3 for storage of empty syringes. The Automated Filling/Packaging Station 4 also includes a conveyor assembly 50 for transporting syringes from storage bin 3 to a plurality of integral sub-stations, including a syringe size inspection station 11 which verifies that the correct syringe has been selected, and a syringe orientation substation 8 next in line to uniformly orient syringes (to account for off-center nozzles). This is followed by a syringe fill/cap substation 5, then a check weight and/or volume substation 6, a syringe label printer and labeler substation 9, and lastly a bag printing and sealing substation 7. The purpose and function of each of the foregoing substations 3-9 will become clearer in the context of a description of the Medication Container Orientation and Log-In Process (step 720), and Batch Fulfillment Process 750.

Medication Container Orientation and Log-in Process (Step 720)

The OSPS system guides the operator in properly equipping and storing each bulk medication container.

Figure 3:
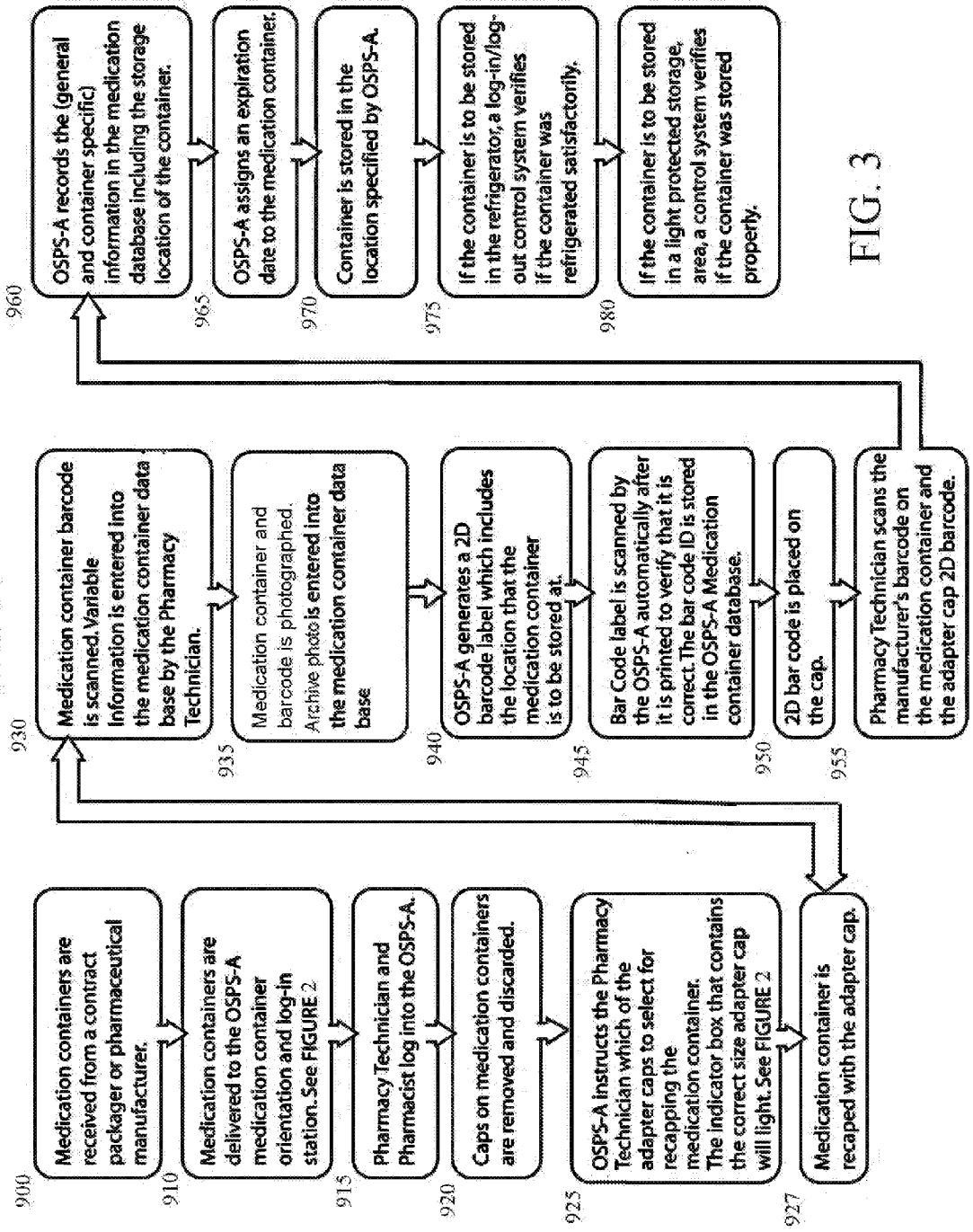
FIG. 3 is a more detailed flowchart of the substeps of the container orientation and login process 720 of FIG. 1.

As shown in FIG. 3, at step 900, medication containers are received from a contract packager or pharmaceutical manufacturer.

At step 910, medication containers are delivered to the OSPS Medication Container Login & Orientation Station 1 (see FIG. 2).

At step 915, the pharmacist and/or technician (operator) logs into the local OSPS computer.

At step 920, caps on medication containers are removed and discarded, with assistance from a capper/decapper 93.

At step 925, the OSPS local computer instructs the operator which adapter cap to retrieve from storage compartments 12 for recapping the medication container. As above, each adapter cap storage compartment 12 may be enclosed by a magnetically-actuable door so that access to each location may be electronically controlled by the local OSPS computer, or illuminated by an LED light, or equipped with a light curtain so that the local OSPS computer can monitor access to the proper location. All these and other suitable forms of user-guidance/selection are considered to be within the scope and spirit of the present invention.

At step 927, the medication container is recapped with the adapter cap, again with assistance from a capper/decapper 93.

At step 930, the manufacturer-provided medication container barcode is scanned by scanner 95A and the derived Product Information is appended to the OSPS database record for that container. Any missing variable information can be entered into the OSPS database record by the pharmacy technician at a data entry terminal 96 in communication with OSPS Computer.

At step 935, each medication container label is photographed using a label photographing station 98 resident at the Medication Container Orientation And Log-In Station 1. The digital photo is automatically appended to the OSPS database record for that container, along with the bar code ID information.

At step 940, the local OSPS computer employs the labeler 97 shown at the Medication Container Login & Orientation Station 1 to generate a 2D barcode label which includes the location that the medication container is to be stored at. The 2D bar code is placed on the adapter cap at step 945.

At step 950, the bar code label is automatically scanned immediately after printing to verify that its contents are correct and the bar code ID is stored in the OSPS database.

At step 955, the 2D bar code placed on the adapter cap, or the base of the medication container, and the pharmaceutical manufacturer's barcode are scanned using a scanner resident at the Medication Container Login & Orientation Station 1.

At step 960, all general and container specific information is recorded in the local OSPS computer database, including the storage location of the bulk container.

At step 965, the OSPS local computer assigns an expiration date to the medication container.

At step 970, the container is placed on a shuttle 52 on the automated storage and retrieval assembly 15 (FIG. 2) and is thereby conveyed to Storage Facility 2 at the location specified by the OSPS local computer.

At step 975 if the container is to be stored in the refrigerator section of Storage Facility 2(b), an optional log-in/log-out control system and procedure is available to verify if the container was refrigerated satisfactorily. This way, if the container is outside of the refrigerated storage area 2(b) more than a specific number of minutes the OSPS local computer will not permit the syringe to be filled from that container, and will alert the Pharmacy Technician to remove and discard that container.

If the container is to be stored in Storage Facility 2 within light protected storage 2(c), at step 980 an optional log-in/log-out control system may be used to verify if the container was stored properly. This way, if the container is outside of the light protected storage area 2(c) more than a specific number of minutes the OSPS local computer will not permit the syringe to be filled from that container.

Fulfillment Process 750

Figure 4A:
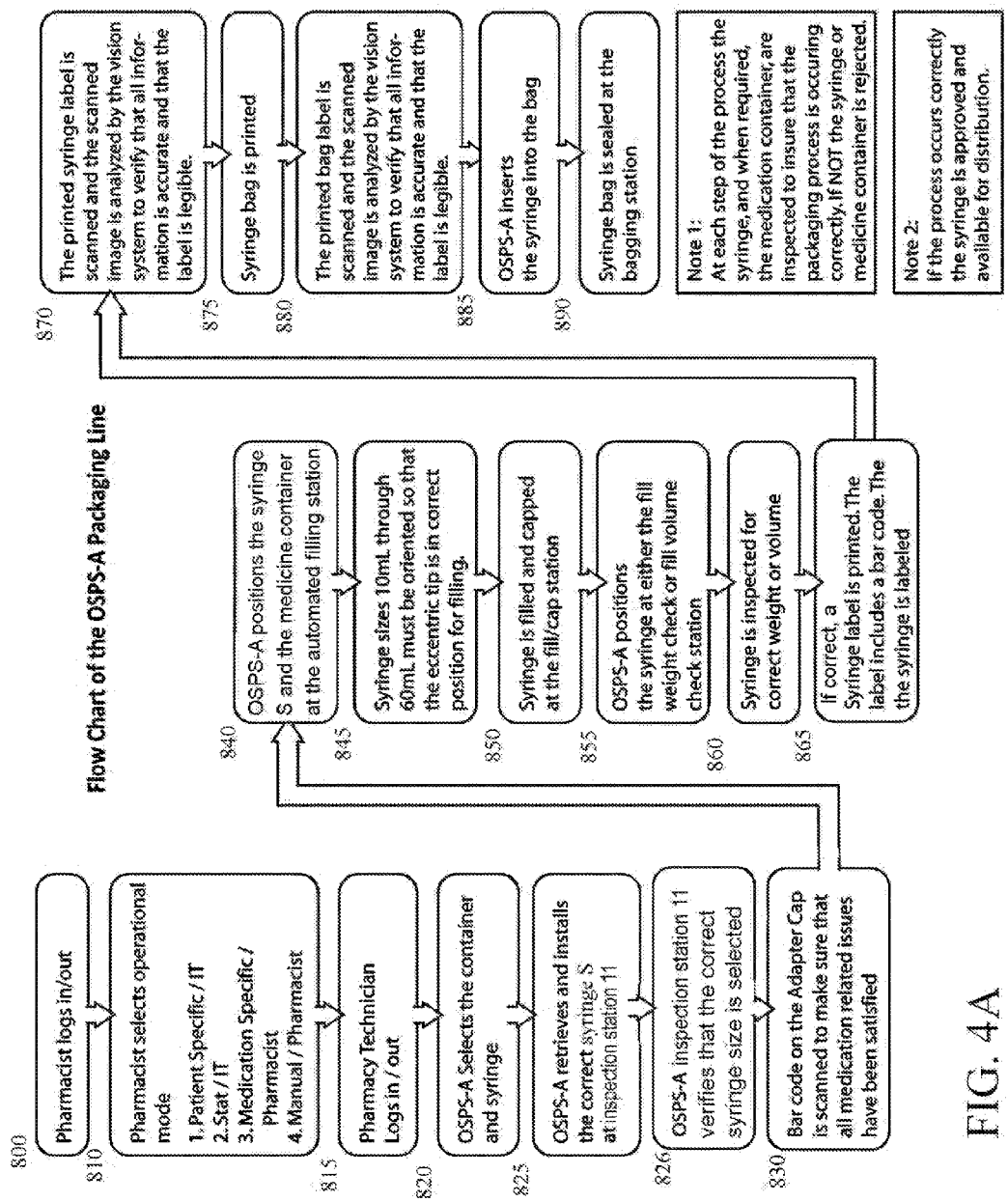
FIG. 4A is a more detailed flowchart of the substeps of the batch fulfillment process 750 of FIG. 1.

With reference both to FIGS. 2 and 4A, at step 800 a pharmacist must log into the OSPS local computer to use the system.

At step 810, the pharmacist selects the desired OSPS operational mode. Currently four modes of operation are envisioned:

1. Patient Specific—Hospital Directed
   a. The Doctor writes the prescription and enters it into the Hospital Host Computer System.
   b. The prescription is reviewed by the Pharmacist. If it is okay, the prescription is sent to the Local OSPS Computer where it is batched. Batches will typically be run 2-3 times a day.
   c. The Local OSPS Computer first sorts all the batched prescriptions in alphabetical order by name.
   d. The prescriptions are then sorted by size of fill from smallest to largest. The total amount of each medication required for that batch run is totaled. The Local OSPS Computer checks to ensure that there is a sufficient amount of product for each medication required to complete the batch.

2. STAT (Rush Order)—Hospital Directed
   a. The Doctor writes the prescription and enters it into the Hospital Host Computer System.
   b. The prescription is reviewed by the Pharmacist.
   c. The prescription order indicates that the prescription needs to be administered soon to the patient.
   d. If the OSPS System 100 is currently being used, the Pharmacist can decide to either stop all current prescriptions being packaged or wait until completion. Either way, the Local OSPS Computer processes the singular rush order.

3. Medication Specific—Pharmacy Directed
   a. This mode allows production-scale filling of a large number of syringes with the same medicine and the same fill volume. Some medication will need to be inventoried in advance of the Doctor's prescription. This mode provides the pharmacist with the opportunity to package certain liquid oral products such as vitamins and popular standard dose medications on a more cost-effective basis than buying them already pre-packaged.
   b. The Pharmacist will automatically enter in a production order for the medication into the Local OSPS Computer.
   c. The Pharmacist will specify the medication name, size of fill, the information that will go onto the syringe label, the information that will go onto the bag that the syringe is packaged in, and the amount of syringes that are to be packaged for that production run.

4. Manual—Pharmacy Directed
   a. Not all hospitals have an existing electronic prescription system installed that permits the electronic transmission of the Doctor's prescription to the hospital pharmacy. Consequently, the OSPS System 100 can be operated on a manual basis whereby the prescriptions are entered into the system under the Pharmacist's supervision.

One skilled in the art should understand that other operational modes include a Patient Priority mode in which all medications/oral prescriptions for a specific patient are processed sequentially before moving on to the next patient. The invention is herein described in the context of Patient Specific—Hospital Directed Mode which is the most typical mode of operation.

At step 815, an operator (pharmacy technician) logs in.

At step 820, the OSPS local computer directs the automated storage and retrieval assembly 15 to select the appropriate medicine container from Storage Facility 2, and an appropriate syringe from storage bin 3 (FIG. 2).

At step 825, the OSPS local computer directs the automated storage and retrieval assembly 15 to retrieve the appropriate medicine container from Storage Facility 2. Similarly, the OSPS local computer directs the shuttle 52 of conveyor 50 to retrieve the appropriate syringe S from its Storage Facility 113.

At step 826, the shuttle 52 shuttles the syringe S into the syringe size inspection station 11 which verifies that the correct syringe has been selected. If it is correct, the conveyor assembly 50 installs it at the syringe fill/cap station 5.

At step 830, the barcode on the adapter cap is scanned to make sure that all medication-related issues have been satisfied (refrigeration, light-sensitive storage, expiration, etc.).

At step 840, the conveyor assembly 50 transports and positions the empty syringe at the syringe orientation station 8. Syringe sizes 10 mL through 60 mL must be oriented so that the eccentric tip is in correct position for filling.

At step 845, the conveyor assembly 50 transports and positions the empty syringe at the syringe at the fill/cap station 5 and the syringe is filled and capped at the fill/cap station 5. The OSPS system automatically fills the syringe with the medicine by insertion of the syringe nozzle into the adapter cap, and withdrawal of the plunger. The system then optionally caps the syringe.

At step 855, the conveyor assembly 50 transports and positions the syringe at the check weight and/or volume station 6 and, at step 860, the syringe is inspected for correct weight or volume. These actions are logged. If the syringe is not the correct weight or volume it is ejected to a reject station.

At step 865, the syringe itself is barcode-labeled at syringe label printer and labeler substation 9 and, at step 870, the OSPS local computer system verifies that the label is printed correctly by scanning with resident scanner 95B. If so, the conveyor assembly 50 transports the barcode-labeled syringe to a bag printing and sealing station 7.

At step 875, a syringe bag is printed/barcoded at bag printing and sealing station 7 and, at step 880, the system verifies that the bag is printed correctly by scanning with resident scanner 95B. If so, at step 885, the conveyor assembly 50 transports and inserts the filled/capped syringe into the barcoded/labeled bag.

At step 890, the syringe bag is sealed at the bag printing/sealing station 7. The packaged syringe can then be distributed to the patient.

At each step of the above-described fulfillment process the OSPS system employs comprehensive track-and-trace inspection/validation of the syringe and, when required, the medication bulk container, to insure that the packaging process is occurring correctly and to compile an audit trail of the current and past locations (and other information) for each syringe.

If the process fails then, as seen at step 760 of FIG. 1, the syringe or medicine container is rejected and no label is printed or applied to the syringe. If the process occurs correctly then, as seen at step 770 of FIG. 1, the syringe is approved and available for distribution. The core method and possible variations are herein implemented in several detailed embodiments of a system suitable for preparing single oral syringe doses. Various alternate embodiments of the invention may omit selected steps (and their performance station) where such is/are not required. The needs of the operating institution and the cost aspect of automating certain steps may direct which steps/stations (if any) are to be performed manually (e.g. syringe selection and loading into the transport device, medication container storage/retrieval) by an operator interfacing with the apparatus and which may be automated.

Figure 4B:
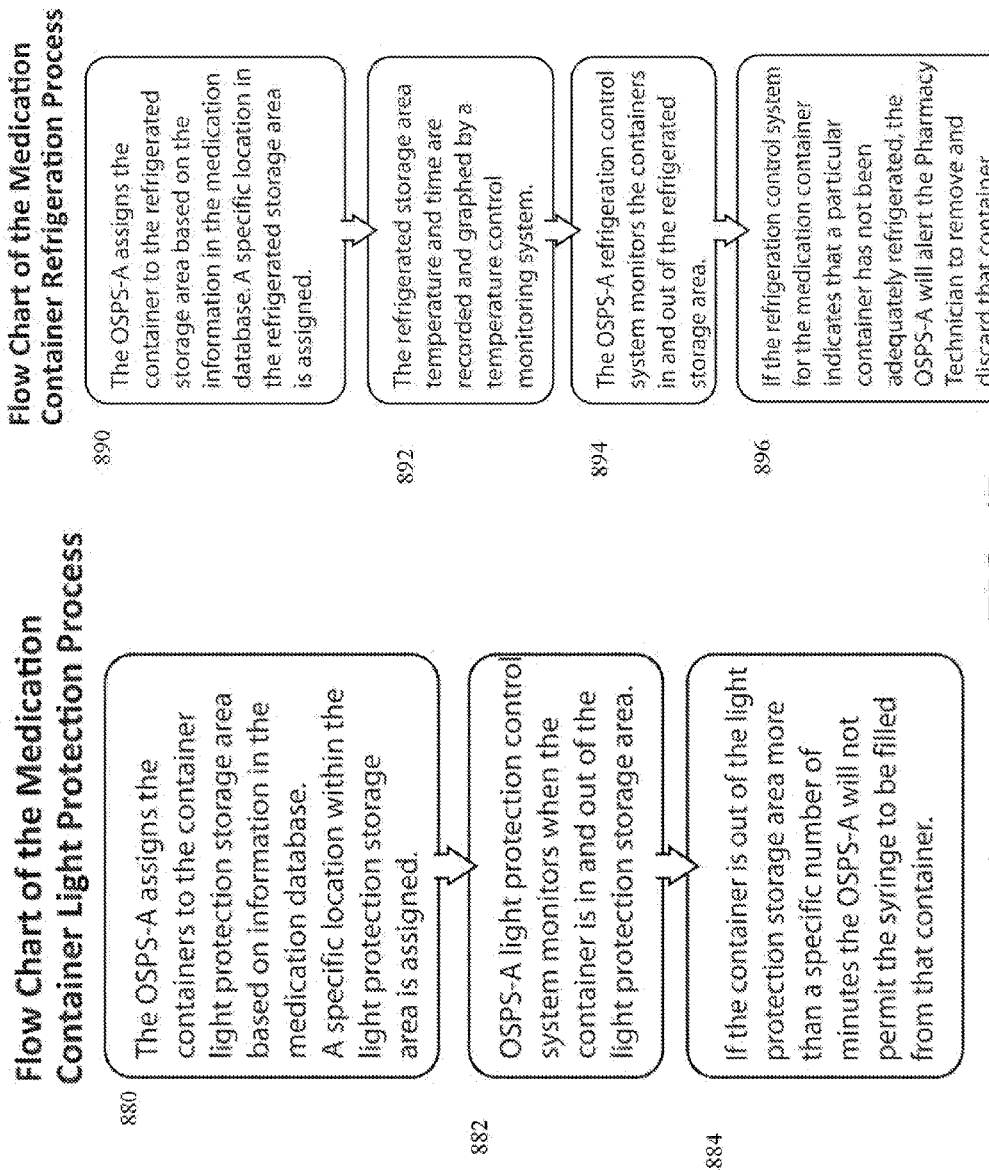
FIG. 4B is a more detailed flowchart of the substeps of the Medication Container Light Protection and Refrigeration Monitoring Processes.

FIG. 4B is a flow Chart of the Medication Container Light Protection Process (left) and Medication Container Refrigeration Process (right) to ensure proper refrigerated and/or light protected storage. During the Medication Container Light Protection Process (FIG. 4B at step 880) the Local OSPS Computer assigns the containers to the container light protection storage area based on information in the medication database. A specific location within the light protection storage area is assigned. At step 882, the OSPS-A light protection control system monitors when the container is in and out of the light protection storage area. At step 884, if the container is out of the light protection storage area more than a specific number of minutes the OSPS-A will not permit the syringe to be filled from that container. During the Medication Container Refrigeration Process (B), at step 890, the OSPS Computer assigns the container to the refrigerated storage area based on the information in the medication database. A specific location in the refrigerated storage area is assigned. At step 892, the refrigerated storage area temperature and time are recorded and graphed by a temperature control monitoring system. At step 894, the OSPS refrigeration control system monitors the containers in and out of the refrigerated storage area. At step 896, if the refrigeration control system for the medication container indicates that a particular container has not been adequately refrigerated, the OSPS will alert the Pharmacy Technician to remove and discard that container.

Referring back to FIG. 2, each station of the pharmacy automation system 100 for oral syringes is described below in more detail.

Medication Container Login & Orientation Station 1

The first station in the process of the present invention is Medication Container Login & Orientation Station 1 at which the bulk medicine is prepared for use in the system 100. Medication Container Login & Orientation (MCLO) Station 1 is a standalone desk unit that provides a facility for inputting needed information into the OSPS database via scanner 95A and data entry terminal 96, applying barcodes as needed via label printer 97, decapping bulk containers 104 at capping/decapping station 93, and refitting them with adapter caps (as will be described with reference to FIG. 5) at capping/decapping station 93. The scanner 95A, data entry terminal 96, and label printer 97 are commercially available components. Capping/decapping station 93 is described below with regard to FIG. 23. Label photographing station 98 is described below with regard to FIG. 24.

MCLO Station 1 is standalone so that it can be positioned as desired. Medicine for oral syringes is provided in liquid form in a factory container with a manufacturer-applied safety cap. An object of the present invention is to be able to insert a syringe nozzle into the containers to withdraw a proper dose of medicine into the syringe. In a fully-automated system 100 such as this, the process is facilitated by removal of the manufacturer's cap and replacement with a specialized adapter cap having a penetrable seal for insertion of an oral syringe nozzle (or alternatively, manufacturer's conforming their packaging such that they provide their products to hospitals with an adapter cap pre-applied). The use of adapter caps (1) allows all medication container sizes/shapes to be used with the OSPS System 100, (2) provides the means for inserting the syringe S into the container in the upside down position and withdrawing the necessary amount of medication without allowing any liquid to leak out of the container, (3) enables the container to be identified, (4) enables the container to be stored, (5) enables the container to be transported, and (6) enables the contents of the container to be protected.

FIG. 5 is a composite view of an adapter cap 210 according to the present invention which is adapted to fit a variety of medicine bottle types and sizes. Despite the variability in OEM medicine bottle types and sizes, the adapter cap 210 affords a consistent external configuration and dimensions, providing an interface between any standard medication container and the present OSPS system 100. It also facilitates insertion of the oral syringe nozzle into the medication containers. As described in detail below, each adapter cap 210 is an annular member defining an internal barrel with an aperture 223 at one end, an elastomeric seal 225 over the aperture for penetration by the nozzle of a syringe S, and opposing flanges 214 separated by a groove 220. An overcap 229 may be provided as a protective cover to the adapter cap 210. The opposing flanges 214 encircle the cap body and define the annular groove 220 there between for positive engagement by the dispensing apparatus 100 so as to enable syringe filling operations. Dual flanges are important as they enable pick-and-place manipulation of the medicine containers, including shaking, though one skilled in the art should understand that some manipulation including shaking and/or staging may be accomplished with only one flange. Each adapter cap 210 is barcoded just after application to a medicine container with a unique identifier number. If desired, one of the flanges 214 may be defined with a peripheral flat area for displaying a bar code 290 or, alternatively, bar code 290 may be located atop the uppermost flange 214 (on the top of the cap). The other flange 214 may also be defined with a peripheral flat area for indexing the orientation of the medicine container 104. One flat area enables orientation of the adapter cap 210 in a known position. The other flat area better presents the identifying information such as a barcode for automated sensing or reading of the information. The flat areas also enable or facilitate automated or manual tightening of the threaded connection between the neck of the container 104 and the cap 210. The barcode flat and the orientation flat are preferably parallel to one another and on opposite sides of the adapter cap 210 and are also longitudinally offset so as to be distinguishable. The known relationship between the orientation flat and barcode flat facilitates automatic positioning and orientation of container with the dispenser and indexing of its angular orientation. In addition to or in place of one or more of the flats, strategically located holes or recesses in the top surface of the cap may be provided. In addition, molded surface features or textures may be provided about the uppermost flange 214 and/or lower flange 214 to provide a gripping surface. One skilled in the art should also recognize that identifying information can be expressed by barcode printing or labeling directly on the cap 210 or the cap may serve as a vehicle to carry an "RFID" tag. The plastic resin used to mold the cap may be formulated to contain an ingredient that would allow direct printing on the cap with either ink or a laser without the need for or use of adhered paper or similar labels. The top of the cap may also be used to affix, print or etch the barcode either by direct printing or adhesive label.

With reference to the middle inset of FIG. 5, an exemplary embodiment of an adapter cap 210 is depicted. Adapter cap 210 comprises a generally annular cap body preferably formed of a polyethylene, polypropylene, polyvinyl chloride or a similar synthetic polymer. The cap body is formed with an annular outer wall 221 for supporting opposing flanges 214, a coaxial annular inner wall 222 for sealing and centering the cap 210 against the outer threaded-neck of the medicine container, and a hub 229 between walls 221, 222. The hub 229 is defined by a central channel for supporting and centering an elastomeric seal 225 within the neck of the medicine container. In addition, an annular wafer seal 226 is formed or attached coaxially within the inner wall 222, spaced slightly therefrom, to produce a seal against the smooth inner-neck of the medicine container. The flanges 214 may be hollowed as shown to conserve material, solid, or may be open around their periphery. Also, the flanges 214, annular outer wall 221, coaxial annular inner wall 222 and hub 229 may be integrally formed (such as by molding), or may be separate but attached as shown. In the preferred embodiment the annular wafer seal 226 is a separate component ultrasonically-welded to the hub 229. The annular inner wall 222 is open at one end and constricted at the other by the inwardly projecting hub 229 which defines a typically circular aperture 223 through the cap body 220 for access to the contents of the medicine container 104 as will be described. The elastomeric seal 225 is mounted in the aperture 223 to create a sealed but penetrable passage for the syringe S nozzle as shown.

The inner wall 222 of the adapter cap 210 may be defined by a simple inwardly-threaded connection for screw-insertion onto the threaded container 104 neck. However, the great variety of manufacturer thread pitches and container 104 neck sizes weighs in favor of a more universal-fit adapter cap 210. This is possible by providing the inner wall 222 of the adapter cap 210 with a series of integrally formed inwardly-directed circular gripping ribs 242 for gripping the neck of a bottle 104 by its threads. As the neck of a bottle 104 is forced into the central void, the ribs 242 engage the threads on the outside of the neck of the bottle and flex slightly to permit the threads to pass. Once past, the ribs 242 spring back toward their original position and press against the neck to engage the threads and secure the adapter cap 210 to the container 104. The variable size of the central void due to the flexure of the ribs 242 permits the adapter cap 210 to accommodate some variation in outside neck diameter and thread finish, and create a fluid-tight seal without the need for a specific thread pitch. The coaxial annular wafer seal 226 abuts the interior of the container 104 neck, centers the adapter cap 210, and adds to the seal against the smooth inside surface of the neck of the bottle 104. Similar to the inner wall 222, the annular wafer seal 226 may also be formed with a plurality of outwardly-directed annular ribs or wipers to improve the seal, or may contain an outwardly-facing O-ring for the same purpose. Again, annular wafer seal 226 is in this case a separate element inserted into the inner wall 222 of the cap body and secured in place by ultrasonic welding or otherwise.

To improve the resiliency of the inner wall 222 and/or wafer seal 226 either/or can be segmented by notches partially interrupting the continuous walls, thereby forming several (preferably eight) "spring finger" segments arrayed about the central axis. The bottom inset of FIG. 5 illustrates this axial array of segments 227 which, if formed in inner wall 222 effectively snap over the threads on the exterior of the neck of the medicine container 104. The serrated segments 227 are first to advance down the threaded neck and align the neck for a better seal with the adapter cap 210 body. The same can be done on the annular wafer seal 226 to improve resiliency, again forming several (preferably eight) "spring finger" segments to abut the interior of the medicine container 104 neck.

Even with the resilient ribs 242 and segments 227 each adapter cap 210 won't fit all container 104 sizes, it is envisioned that several (approximately eight) sizes of adapter caps 210 will be needed.

The elastomeric seal 225 is fitted within the aperture 223 of the hub 229. In its simplest form the elastomeric seal 225 may be a resilient, penetrable membrane with a small hole or slot (such as a pinhole) punched at its center, and preferably formed of silicone or other rubber. The hole in the seal 225 expands as the tip of a syringe S is inserted to permit pressurization of the container 104 and/or filling of the syringe (by vacuum) as described below. On withdrawal of the syringe tip the resilient elastomeric seal 225 returns to its original shape closing the hole and preventing leakage of the fluid contents of the bottle 104. However, a flat elastomeric seal 225 with a hole or slot has been found to drip slightly.

To prevent dripping, a preferred embodiment of the elastomeric seal 225 is shown in the right-most inset of FIG. 5, which improves the engagement with the nozzle of the syringe S. Seal 225 is formed with a hollow cylindrical section 231 circumscribed by a flange 232 for mounting within (or to) the coaxial annular inner wall 222 of the adapter cap 210 body. The cylindrical section 231 leads to a pronounced duck-bill protrusion 233 that tapers to a distal tip, with aperture 223 (preferably slotted) continuing out through the duck-bill protrusion 233. The duck-bill protrusion 233 serves as a flap valve against the nozzle of the syringe S and expands to receive the nozzle of the syringe S.

The duck-bill configuration is advantageous because it creates a seal around the syringe S nozzle prior to the nozzle forcing open the duck bill slit. Likewise, upon exit, the duck-bill slit closes prior to the syringe nozzle breaking its seal against the interior. This tends to self-relieve pressure and prevent dripping.

The adapter cap 210 is typically applied to the container 104 and inserted into the Storage facility 2 (FIG. 2) in an upright orientation as shown. The adapter cap 210 allows the attached medicine container 104 to be automatically staged by the upper and lower flanges 214 (though as stated above staging may be accomplished with only one flange), and thereby gripped at the syringe fill/cap station 5, shaken (when needed), and inverted 180 degrees into a fill position (as in FIG. 5 middle inset) for upward insertion of the syringe S. Inversion allows the fluid contents to be collected at the adapter cap 210 under force of gravity. The type of adapter cap used with the present invention may depend on the features/options chosen by the customer for their desired level of automation. For example, if the system is fully automated then the adapter cap must have a flange for manipulation, and hence an adapter cap 210 is required such as shown in FIG. 5 to incorporate flange(s) 214. However, semi-automatic operation is possible in which the medicine containers may be loaded manually. One skilled in the art should understand that the above-described filling and capping station 200, being manually loaded with medicine containers, does not necessarily require the dual-flanged adapter cap 210 described previously, or duck-bill seal 225 as described previously. Any manufacturer-supplied adapter cap may be used provided that it is equipped with an elastomeric membrane seal for the syringe S nozzle, most preferably a duck-bill embodiment 225 as shown in FIG. 5. Thus, any conventional cap, such as Baxa's AdaptaCap™ bottle adapter cap may be used (as shown in U.S. Pat. No. 4,493,348 referenced above) and simply modified or equipped by the manufacturer or aftermarket with an elastomeric seal such as 225. Moreover, any conventional cap can be retrofit with an overcap to provide one or two flanges, when desired. FIGS. 6-7 are composite views of two alternate embodiments of the adapter cap 510, 610 adapted for retrofit to an existing medicine container cap. Both designs comprise a press-over plastic cap that allows existing medicine container caps to be used in an automated or semi-automated packaging system, adding the penetrable elastomeric (e.g., duckbill) seal and flang(s) thereto.

More specifically, FIG. 6 illustrates how a conventional medicine container cap 335 is outfitted with an overcap 525 to provide a flange 527 and, in addition, a retrofit duckbill seal 225. The seal 225 is attached as shown by creating a ¼" diameter hole through the top of the cap and attaching the elastomeric seal 225 in that opening. A medicine container bottle is then attached. The overcap 525 comprises an annular cap that is press-fit down overtop the conventional medicine container cap 335. In the illustrated embodiment, the overcap 525 is formed with inwardly protruding flanges 535 about the bottom edge to lock it in place. For medicine containers equipped with a spout cap 528 attached by a tether 529, a slot 537 may be defined ingressing from the bottom edge of overcap 525 to a right angle to accommodate the tether 529, the right-angle slot providing a twist-lock feature to secure the overcap 525 thereon. In this case the overcap 525 may be barcoded up top as shown at (A), or on the bottom of the medicine container. For medicine containers not equipped with a spout cap/tether, the spout cap 528 attached by a tether 529 may be molded to the side of the overcap 525.

FIG. 7 shows yet another embodiment in which a spout cap 628 is molded to overcap 625 by a resilient arm 629 that is attached at a plastic hinge. A plastic leaf spring 627 (also molded) straddles beneath the hinge to provide a spring-biased closure action. The inner chamber of overcaps 525, 625 may be molded with an annular groove 630 (see FIG. 7(B)) about the top to seat a rubber or silicon washer, thereby preventing seepage. Another means for preventing seepage is to co-mold an elastomeric seal, in the form of an o-ring or washer, within the annular groove 630.

In light of the foregoing description of the potential use of a conventional (such as a Baxa® adapter cap, the following are optional modifications thereto (a) tethered nozzle closure or hinged nozzle closure;
(b) co-molded a washer on the underside of the cap that touches the lip of the container, or washer attached to the underside of the cap to provide a leak-proof, air tight seal between the underside of the cap and the lip of the container (note that the underside of the cap will need to retain this washer).
(c) increased-diameter opening (syringe port) to allow for a duck bill to be inserted and held in place by the cap
(d) one or two flanges for orienting the hinged cap and also to transport, handle and store the medication bottle. The flange(s) may be integrally molded or attached separately (possibly snap-fit in place) and if needed, welded to the cap. The type of cap used with the present invention will depend directly on the features/options chosen for the present system. For example, if the system is fully automated then the medicine container cap must have a flange for manipulation, and hence an adapter cap 210 is required such as shown in FIG. 5 to incorporate flange(s) 214. However, for semi-automatic operation in which the medicine containers are loaded manually the flange would not be used because it is not required, adds cost to the cap, makes the bottle less stable, and causes the bottle to occupy more space which is a disadvantage when storing the containers. Thus, two versions of the adapter cap are required—one with the flange (for automatic operation) and the other without (for semi-automatic operation).

Referring back to FIG. 2, at MCLO Station 1 a number of bins 12 are provided for storing various sizes of adapter caps 210 as needed to fit all standard container sizes. As described above in steps 910 through 965 (FIG. 3), the OSPS system 100 automatic medicine container selection, return process, and syringe S selection is fully automated, but adapter cap 210 selection is system-guided. For example, each adapter cap storage compartment 12 may be enclosed by a magnetically-actuable door so that access to each location may be electronically controlled by the local OSPS computer, or illuminated by an LED light, or equipped with a light curtain so that the local OSPS computer can monitor access to the proper location.

OSPS system 100 implementation of the fully-automated container 104 selection process employs a software module resident in the local OSPS computer that relies on all three of the information components stored in the OSPS system database: 1) product information from the manufacturer or other external sources describing the medicines and their containers (size, dose, handling requirements, etc.); 2) prescription-specific information from the hospital identifying the prescription details and patient to receive it; and 3) OSPS runtime information such as the amount of medicine previously taken from a given bulk container. Specifically, patient-specific information from the hospital identifying the prescription details is compared to product information from the manufacturer or other external sources to determine the appropriate medicine to retrieve. The software module ascertains from the patient-specific information the appropriate amount of medicine to retrieve. This is compared to OSPS runtime information (the amount of medicine previously taken from the bulk containers 104) to determine the specific container 104 to retrieve. The location of that container 104 is ascertained from the scan of the container 104 and pre-labeled adapter cap 210 at scanning station 95A, and the ensuing storage location in Storage facility 2 which was assigned automatically by the local OSPS computer. Given the desired container 104 location, in one embodiment a shuttle 52 translates along the conveyor assembly 50 and employs an on-board gripper 51 to retrieve the container from the Storage facility 2. Other embodiments of the conveyor assembly 50 are described below which employ alternatives to shuttle 52.

In operation, and as described previously with regard to FIG. 3 (medication container orientation and log-in process step 920), the OEM caps on medication containers 104 are removed and discarded at capper/decapper 93, the OSPS local computer instructs the operator which of the adapter caps in storage 12 (FIG. 2) to select for recapping the medication container 104 (step 926), the operator retrieves the proper adapter cap 210 under system 100 guidance and applies it at capper/decapper 93. The labeler 97 generates a 2D barcode label which includes the location in Storage facility 2 where the medication container 104 is to be stored. The operator places the 2D bar code on the adapter cap, and the 2D barcode on the adapter cap is scanned by scanner 95A. All general and container specific information derived by scanning or supplemental data entry at data entry station 96 is recorded in the local OSPS computer database, including the storage location of the bulk container 104 in Storage facility 2 and the expiration date of the medication container.

The operator places the medication container in the label photographing station 98 described below with regard to FIG. 24, and the container label is photographed. The digital photo is automatically appended to the OSPS database record for that container, along with the bar code ID information.

The operator then loads the container onto another gripper/shuttle 52 which translates along the conveyor assembly 50, and the conveyor assembly 50 moves and stores the container in the Storage facility 2 location assigned by the local OSPS computer. If the container is to be stored in light protected storage 2(*c*) or refrigerated storage 2(*b*) the track-and-trace software ensures compliance. Later, when needed to fulfill a batch of oral syringe prescriptions the local OSPS computer will actuate a shuttle 52 to retrieve the desired medicine from the Storage facility 2 with adapter cap 210 applied, gripping it within the groove 220 and loading it into a product interface 70 (described below) at the fill/cap station 5. The medicine may be verified by a resident scanner 95B at the Automated Filling and Packaging Station 4 as to proper content, available fluid volume and other attributes before being loaded at the product interface 70.

The first substation in the Automated Filling and Packaging Station 4 is, according to the present invention, a storage bin 3 for storage of empty syringes. The syringe storage 113 preferably incorporates a separate syringe compartment or shelf for each size of syringe that the system anticipates needing in the course of a production run. In the illustrated embodiment, the storage bin 3 is a top-loading gravity-fed dispenser with multiple fixed or adjustable dividers to allow separation of syringes according to size. The inclined chute gravity-feed configuration positions each size of syringe for easy pick-and-grab selection by the gripper 51 of shuttle 52. As with medicine container 104 selection, the OSPS software ascertains from the patient-specific information the appropriate dose of medicine to determine the specific syringe S size to retrieve. The location of that syringe S is ascertained from the database, and the exact syringe S location in syringe storage 113 is presented to the operator who retrieves it from the syringe storage 113. In still other embodiments the syringe S may be automatically ejected to the shuttle 52 under control of the local OSPS computer. The OSPS syringe-selection software module calculates the most appropriate syringe S size based on the required prescription information dosage, the known volume of the syringe selections (the following standardized oral syringe sizes: 0.5 ml, 1 ml, 3 ml, 5 ml, 10 ml, 20 ml, 35 ml, and 60 ml), identifies the syringe size to accommodate the fill volume of the prescription, and moves the shuttle 52 accordingly until its gripper 51 can retrieve the syringe from the proper magazine.

The second substation in the Automated Filling and Packaging Station 4 is the syringe size inspection station 11 which verifies that the correct syringe has been selected. The syringe size inspection station 11 is described more fully below with regard to FIG. 25.

The next substation in the Automated Filling and Packaging Station 4 is a syringe nozzle tip orienter 8 for orienting syringe nozzles to a common position. This is necessary as many syringe nozzles are offset from center. The syringe nozzle tip orienter 8 indexes the orientation of the syringe nozzle to the same angular position when the syringe is in the fill position.

Figure 8:
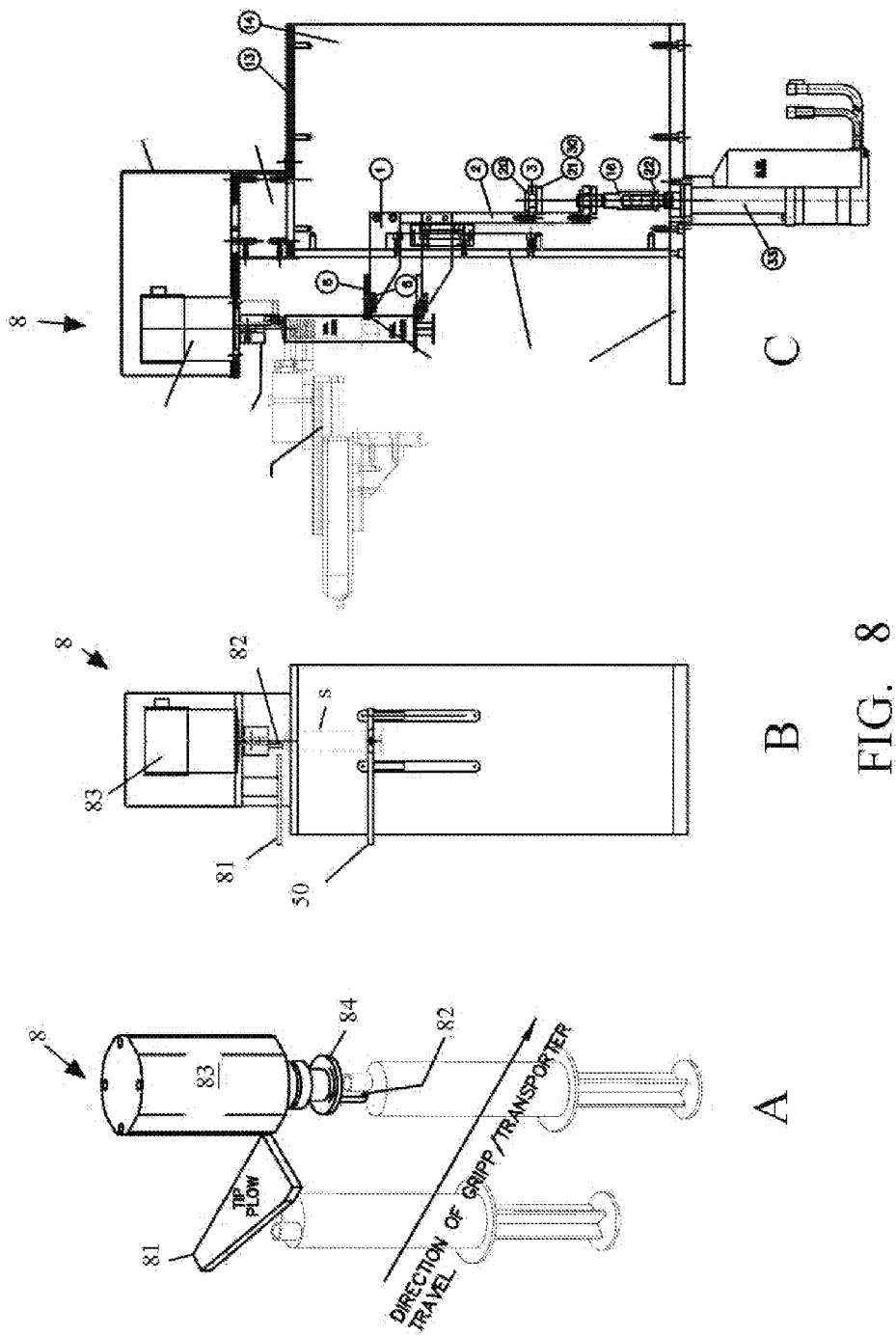

FIG. 8 includes a conceptual perspective illustration at A of how the syringe nozzle tip orienter 8 works, as well as a detailed front view B and side view C. As seen at A, the conveyor assembly 50 transports the empty syringe to the syringe orientation station 8 in the direction shown such that the nozzle tip catches a plow 81. With the syringe nozzle tip rubbing along plow 81 the gripper 51 of the conveyor 50 allows free rotation of the syringe, pushing the nozzle tip outward and serving to prevent the syringe nozzle tip from crashing into nozzle tip orienter 8. With nozzle tip clear, the syringe S continues until positioned under a rotator finger 82. The rotator finger 82 is driven by a servomotor 83 which is under control of the local OSPS computer. The rotator finger 82 is a downwardly-protruding pin mounted offset on a rotating hub 84 attached to the servomotor 83 shaft. Once the syringe is centered underneath, the gripper 51 of the conveyor 50 stops, and the servomotor 53 is activated such that the rotator finger 82 makes one complete revolution. The finger 82 catches the nozzle tip at some point along its revolution and urges it into an indexed position, thereby presenting the syringe tip at an exact known angular position (e.g., 12 o'clock). The gripper 51 closes tightly to secure that indexed position thereby facilitating alignment with the filler centerline.

The fourth substation is the syringe fill/cap station 5 for filling and capping the syringes S (see FIG. 2). The system 100 transfers a medicine container 104 into the fill station 5 from a shuttle 52 of conveyor 50 (after picking the appropriate container from its designated location in Storage facility 2) by loading it into a carousel product interface 70. Meanwhile another shuttle 52 positions an empty syringe S (step 840) at the syringe fill/cap station 5.

Carousel product interface 70 rotates the medicine container around into a loading carriage 81 at the syringe fill/cap station 5. The product interface 70 stages multiple medicine containers just prior to the filling process in order to minimize the time required when transitioning from one medicine container to the next. The loading carriage 81 engages the container 104 by the grooves 220 of the adapter cap 210 and inverts it into a fixed upside down position and orientation over the syringe S (see FIG. 5 middle inset) to facilitate the filling of the syringe S. The system automatically fills the syringe S with the medicine by inserting the syringe nozzle into the adapter cap 210 followed by a calibrated withdrawal of the plunger (to be described). As seen in FIG. 2 an integral capper 147 caps the syringe at the filling station, after which it is returned to the conveyor 50.

The fifth substation is an inspection station 6 which at least comprises a check-weigh scale. The system 100 uses it to weigh and/or inspect the filled syringe S to verify the syringe is filled as intended, and the System 100 accepts or rejects the weighed/inspected syringe. The OSPS software calculates the target weight based on the fill size in cc's and multiplies by the specific gravity to derive weight. The specific gravity of each medication is stored in the OSPS database along with the percentage+/-% deviation that is acceptable for the actual fill weight. If the actual fill weight is in the target range, it is accepted. If not, it is rejected.

More preferably, inspection station 6 is a vision inspection station (alone or in combination with check weigh scale) to ascertain fill volume.

Figure 9A:
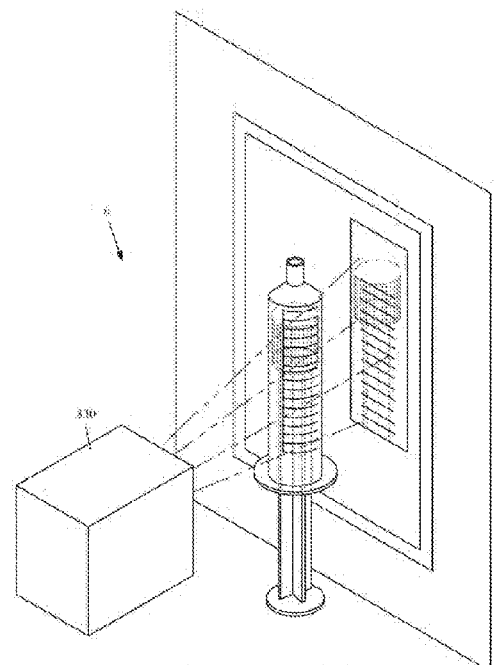
FIG. 9A is a perspective view of an exemplary vision inspection station 6, and at FIG. 9B shows the sequence of operation.

FIG. 9 at (A) shows a perspective view of an exemplary vision inspection station 6 in which the syringe fill volume is inspected by a CCD imager 330 that optically detects, by image analysis, if the syringe S plunger is at the correct location, if the volume above the plunger and below the syringe tip is filled with product, and/or if there are any bubbles in the product. If the syringe volume inspection device 6 determines that the syringe is filled to the correct volume with an acceptable amount of bubbles, it will be accepted. Otherwise, it will be rejected.

Figure 9B:
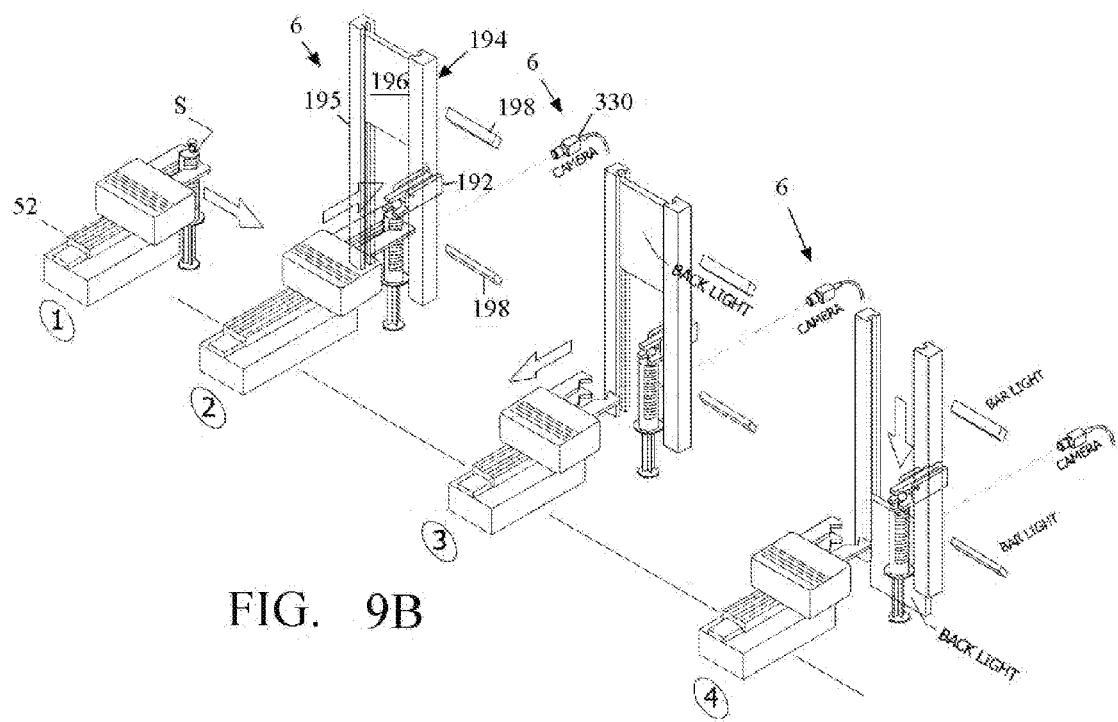

FIG. 9(B) shows the sequence of operation in a preferred embodiment. First, the shuttle 52 of conveyor 50 carries the syringe S into the vision inspection station 6 and places and releases it in a gripper-bracket 192 that establishes and maintain a fixed 'Reference Point' that is ascertainable for all syringes S. Preferably, the reference point is just below the syringe tip and at the intersection of the top of the syringe body. A CCD imager 330 resides behind the conveyor 50 and gripper-bracket 192. Thus, in order to effectuate the proper backlighting, the shuttle 52 hands the syringe S off to gripper-bracket 192 through a guillotine-style backlight assembly 194 comprising a pair of spaced-apart vertical rails 195 and an articulating backlight panel 196 that moves up and/or down within rails 195. Frontal lighting may also be provided by LED light bars 198. After the shuttle 52 hands the syringe S off to gripper-bracket 192 the backlight panel 196 is lowered into position, so that it lies directly behind the syringe S in the optical path of CCD imager 330. With back-and-frontal lighting on, the CCD imager 330 images the syringe S from the 'Reference Point' downward to the seal ring of the plunger. This results in a numerical dimension for the specific syringe size and relative to the prescribed dose. The reading is compared by the OSPS computer to a pre-determined number associated with both the syringe size and every increment on the syringe. For example, if a 10 ml dose is prescribed the database recommends a 20 ml syringe if properly filled, and the imaged dimension will read 32.75 mm or 1.289". The inspection station 6 also checks for excess bubbling. Any voids or bubbles are interpreted as a mixed pixel count in either light or dark depending on the opacity of the medication from our data base. Any voids or bubbles will be interpreted as a mixed pixel count in either light or dark depending on the opacity of the medication from the data base. In the event of miss-match of pixel color or shading within the fill zone the error is flagged. The fill accuracy is preferably +/−5% of target. The bubble void percentage is preferably at +/−2½% of mismatch. After visual inspection the backlight panel 196 is raised, and the shuttle 52 retrieves the syringe S from gripper-bracket 192. In case of failure the pharmacist will make a decision to either pass or fail the filled syringe S.

The sixth substation is a flag label printer/applicator 9 as seen in FIG. 2. After inspection of the syringe S at inspection station 6, if no defects are found, the shuttle 52 of conveyor 50 inserts the syringe into syringe label printer 9, which is a commercially available flag label printer/applicator. As described above relative to FIG. 3 (step 865), the syringe label printer 9 prints a syringe label and inspects it for content accuracy just before applying it to the syringe S. The labeler is in communication with the local OSPS computer and automatically prints self-adhesive labels bearing information regarding the prescription such as the contents of the syringe (medicine type, concentration, dosage, expiration, scheduled administration, etc.) and its intended recipient (name, room number, etc.) along with a bar code identifying a central record of this information in the OSPS database. The label includes a 2D barcode though other labels such as RFID may be used. The label is adhered to the syringe barrel using known application methods. In one such embodiment, the label is supported by hinged arms of the printer/applicator 9 and held by vacuum pressure while the applicator advances to envelope the syringe barrel with the hinged arms coming together to join the label as a flag to the barrel of syringe S. A portion of the label around the barrel must be transparent to permit dosage markings of the syringe to be clearly visible.

The seventh substation is a bag printing and sealing station 7. The bagging station 7 is a commercially available Hand Load Printer/Bagger for hand load labeling and bagging applications. It is networked to the local OSPS computer to automatically print the bag in which the syringe S will be packaged. The bag is printed with information regarding the prescription such as the eventual contents of the syringe (medicine type, concentration, dosage, expiration, scheduled administration, etc.) and its intended recipient (name, room number, etc.) along with a bar code identifying the same content. After printing a bag, the system inspects the print on the bag to make sure that it is correct. If so, the system places the filled/capped syringe S in the bag and the bag is then sealed.

If all the steps are completed correctly the syringes are distributed for administration to the patient.

One skilled in the art will recognize that certain steps may be completed in various alternate sequences to achieve the same result, and features may be modified or eliminated as a matter of design choice.

With combined reference to FIGS. 1-7 and additional reference to other drawings a detailed description of an embodiment of the present invention and certain alternatives is herein provided.

At initial MCLO Station 1 an operator prepares bulk medicine containers for use at the automated syringe fill/cap station 5. Preparation entails applying an adapter cap 210 onto the neck of the bottle or container to enable the system to engage and manipulate the container 104 during the dispensing process as will be described. Again, each adapter cap 210 includes a unique identifying number, for example, in barcode format. Preparation of the container 104 also includes scanning, verification and recordation of adapter cap 210 information, scanning, verification, photographing and recordation of container 104 label information including content information (name, manufacturer, full volume, concentration, etc.), batch or production information and expiration information, and association of the unique adapter cap 210 number with its assigned container 104 in a medication track and trace database. Various other parameters for each medicine can be associated with each record in the database such as the maximum flow rate at which a certain medicine can be withdrawn from its storage container (i.e. to prevent cavitation/inaccurate fills), the storage temperature (ambient or refrigerated), the required frequency of shaking/agitation of each medicine to keep any particulate matter properly suspended/distributed (e.g. between each syringe fill dispense cycle or only at the start of a series of syringe fill dispense cycles). As an example, each barcode (or possibly RFID tag or other label) preferably references the following information:

Batch number
Expiry date
Storage instructions
Product name
Strength
Name of the active ingredient(s)
Dose form
Warning statements
FDA number
Product need to be shaken before use? If so, how often?
Product need to be refrigerated before use? If so, temp?
Volume of original bulk medication container?

The information available from the pharmaceutical manufacturer's barcode on the medication container varies from manufacturer to manufacturer. The operator is prompted to enter any missing data directly into the computer data entry terminal 96 at MCLO Station 1. The information from the pharmaceutical manufacturer's barcode label plus the variable information is stored in the medication container database which is linked to the medication container by the adapter cap barcode label. The adapter cap 210 identifying number is linked to the container 104 to which it is attached in the medication track and trace database. It is also important that each container 104 is marked in both human and machine readable forms (i.e. text, barcode or RFID tag) as to the type and concentration of the medication it contains along with various other information, to enable visual inspection.

The containers 104 are typically manufacturer-supplied although custom containers may be used for purposes of the present system. If the storage containers 104 are provided by the manufacturer, 20 mm, 24 mm, and 28 mm neck diameters are typical. The bulk containers may be provided in a specified, standardized format by the manufacturer, or the medicines may be refilled into standardized containers onsite.

If a custom storage container 104 is used the neck diameter is a uniform, known size. In either case, the storage containers 104 may be retained in an upright or inverted position and are preferably equipped with adapter cap 210 that allows dispensing while preventing air infiltration that leads to premature spoilage of the contents. Proper adapter caps 210 are either substituted for the manufacturer's onsite or supplement the manufacturer's cap. The medicine containers are moved on shuttles 52 along conveyor 50 into Storage Facility 2, which may be proximate the Automated Filling and Packaging Station 4. Referring back to FIG. 2, the prepared medicine container 104 is returned with its adapter cap 210 to the medicine Storage Facility 2 where it remains until called for. The system software monitors the contents of the medicine Storage facility 2 in terms of both identity of the prepared medicines available to be dispensed and the quantity of each medicine. The content of the Storage facility 2 is continually updated as the medicine is dispensed and the system is able to predict, based on current pending prescription and historical dispensing information, when the current available container of any given medication will be empty so as to advise the operator to prepare a replacement quantity of such medicine prior to emptying the existing container. Medicines exceeding their expiry dates are also identified by the system to be discarded by the operator.

When called for, the medicine containers are likewise retrieved on shuttles 52 along conveyor 50 from Storage Facility 2 and are shuttled into the Automated Filling/Packaging Station 4. It should be apparent that there may be separate independent conveyor 50 tracks and multiple shuttles 52, at least one for moving medicine containers from Storage Facility 2 into the Automated Filling/Packaging Station 4, one for moving medicine containers from Storage Facility 2 into the Automated Filling/Packaging Station 4, and one for moving syringes S along the substations of the Automated Filling/Packaging Station 4. In the preferred embodiment, the conveyor 50 for moving syringes S along the substations of the Automated Filling/Packaging Station 4 is broken into two independent sections each bearing movable shuttles 52, with a handoff there between. This speeds up the process.

Figure 11:
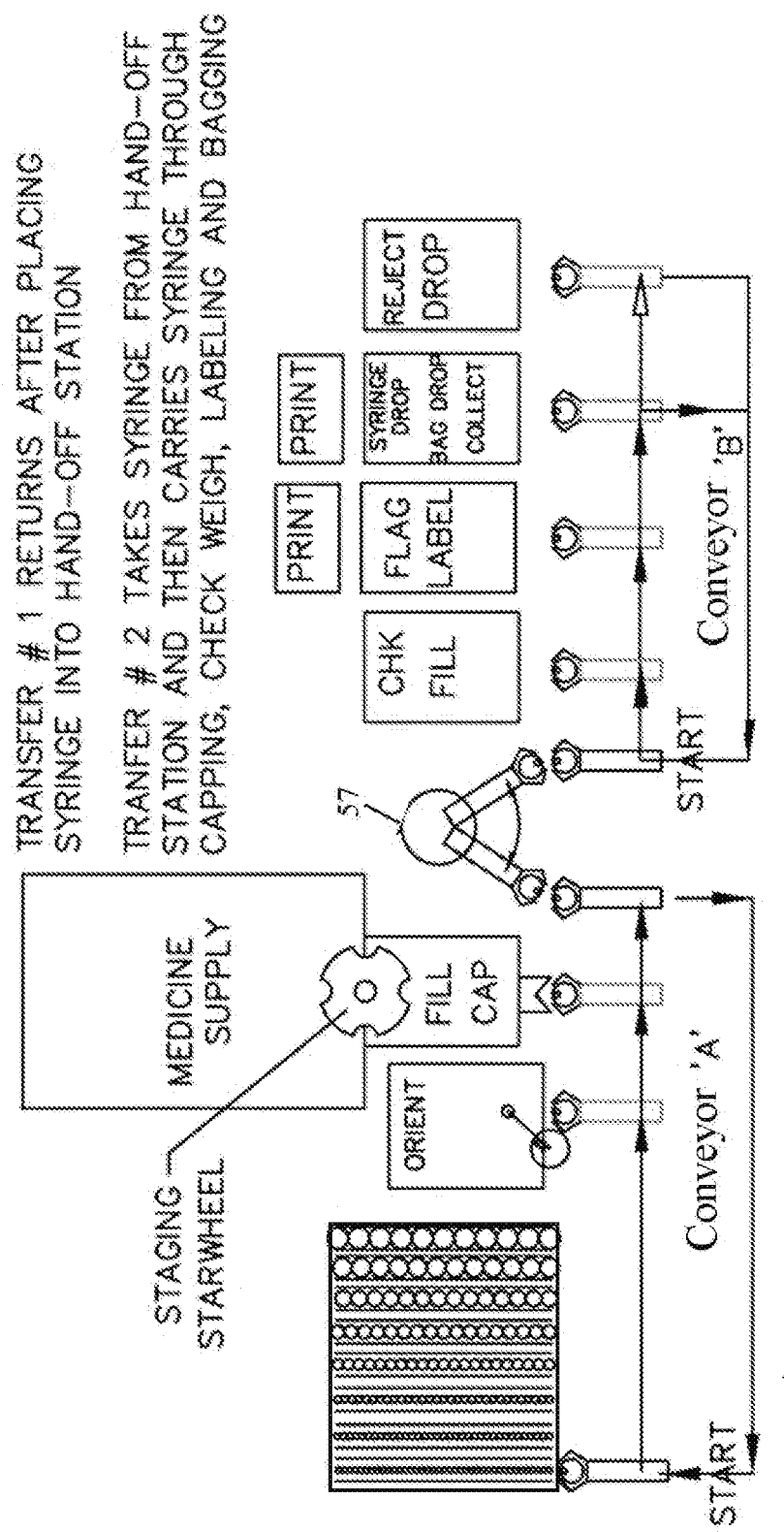
FIG. 11 is a drawing of the sectionalized syringe conveyor 50 for shuttling along the Automated Filling/Packaging Station 4, with two independent sections "A" and "B" each bearing one movable shuttle 52.

FIG. 11 is a perspective drawing of the sectionalized syringe conveyor 50 for shuttling along the Automated Filling/Packaging Station 4, with two independent sections "A" and "B" each bearing one movable shuttle 52, and a handoff turret 57 between sections. A shuttle 52 moves along conveyor section A to pick a syringe from syringe storage 113, move it into the nozzle tip orienter 8, and then into the syringe fill/cap station 5, after which it hands the filled/capped syringe S off to the handoff turret 57. The handoff turret 57 simply transfers the filled syringes for access by the shuttle gripper 51 of conveyor section "B", whereupon it continues through the remaining substations. The advantage of this configuration is that the shuttle 52 in section "A" is free to return for filling another syringe S while the shuttle 52 in section "B" completes the printing/inspection and bagging operations, effectively reducing cycle time by 50%.

After a shuttle 52 picks a syringe from syringe storage 113, it is moved into the nozzle tip orienter 8 and then into a staging area in the syringe fill/cap station 5.

Figure 10:
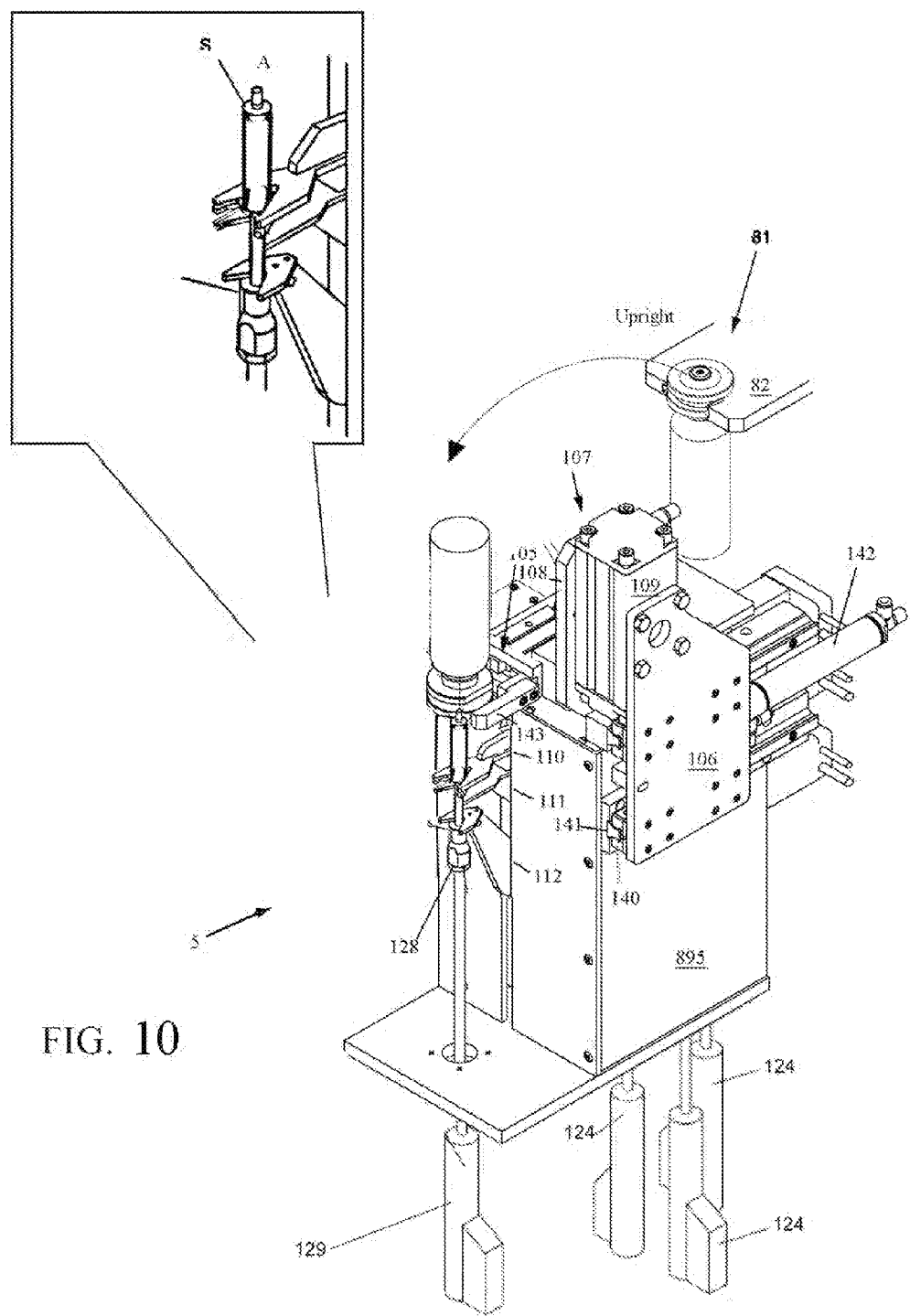
FIG. 10 is an enlarged perspective view of an automated syringe fill station 5 for filling the syringes S.

FIG. 10 is an enlarged perspective view of an automated syringe filling/capping station 5 for filling and capping the syringes S. Syringe S is automatically transported into the staging area by conveyor shuttle 52 and the loading carriage 70 of the syringe fill/cap station 5, preferably with the plunger partially withdrawn from the barrel. Once in the fill position the syringe is engaged by a series of arms, upper 110, middle 111 and lower 112, that grip and operate the syringe S in order to effectuate the filling process.

At the same time, the system 100 loads a medicine container 104 into the fill station 5 by a shuttle 52 of conveyor 50 picking the appropriate container from its designated location in Storage facility 2 and loading it into a carousel product interface 70 which in turn stages the container around into the container gripping apparatus 81. The container gripping apparatus 81 shakes the container when necessary, then effectively flips the container 104 from the home position (A) shown about a 180 degree arc to an inverted fill position (B) out front (as per arrow). Once inverted in the fill position, an oral syringe S is advanced into the elastomeric seal 225 of the adapter cap 220 and is sealed therein (see FIG. 5). The oral syringe may be entirely evacuated such that its plunger is advanced all the way into its barrel or the oral syringe may have a calibrated amount of a gas (such as air or nitrogen) in front of the plunger in the barrel. The syringe plunger may be withdrawn to draw the fluid into the barrel. Where a gas is present in the syringe, the plunger may be first advanced so as to force the gas into the container 104. The plunger is then withdrawn to draw the fluid into the syringe. Introduction of the gas into the container 104 slightly pressurizes the container initially and prevents the development of negative pressure within the container which would inhibit fluid flow. When the syringe is filled to the proper volume it is withdrawn.

Figure 12:
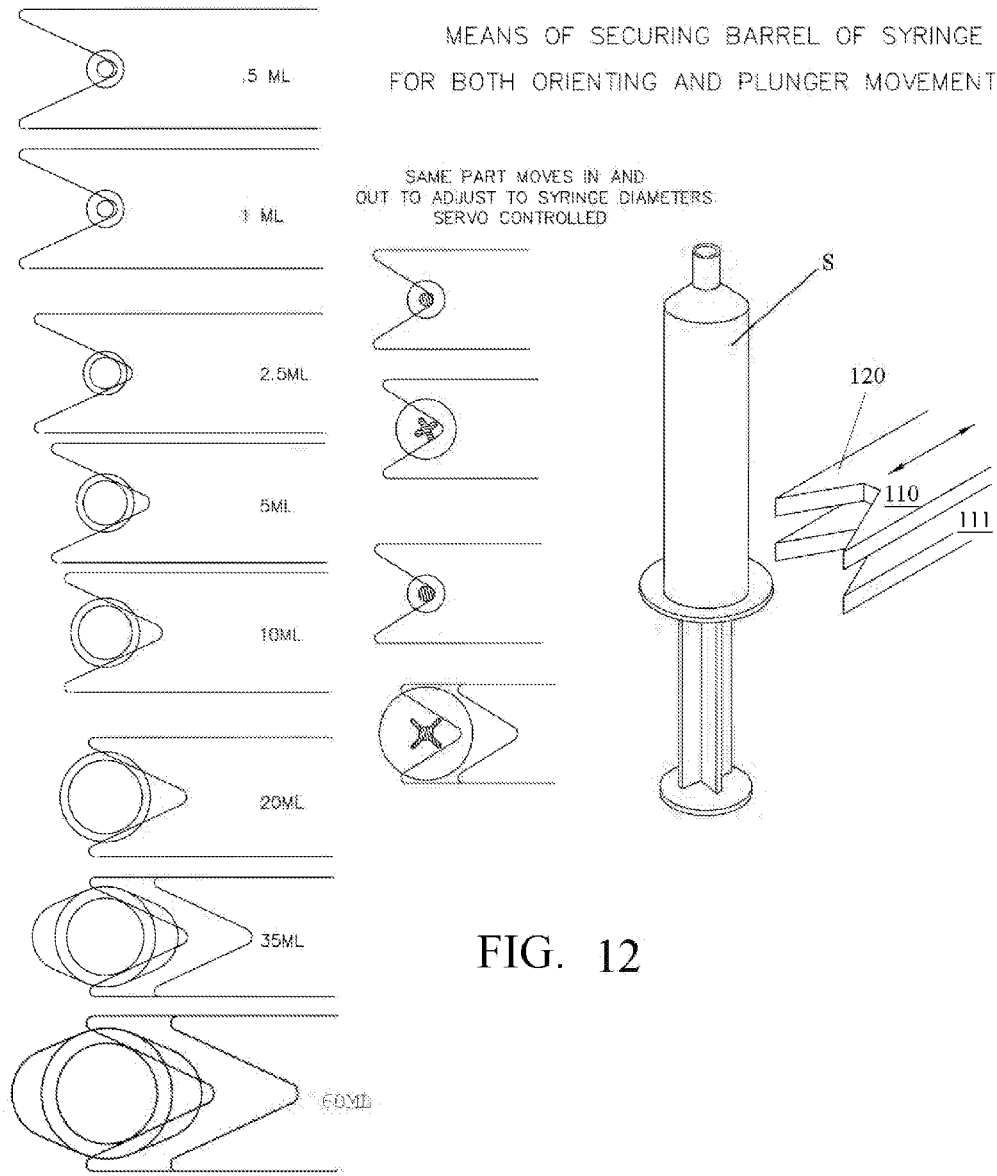
FIG. 12 is a composite view of the syringe gripping arms 110, 111 terminating in a pair of fork shaped fingers 120 that form a horizontally oriented "V" shaped opening.

As seen in FIG. 12, each of arms, upper 110, middle 111 and lower 112, terminates in a pair of fork shaped fingers 120 that form a horizontally oriented "V" shaped opening to engage the syringe barrel and plunger cross sections regardless of the size of these elements. Each arm is independently servo controlled and slideable in both an up-down direction and a horizontal forward-back direction to facilitate engagement with and operation of the syringe and plunger. The capability of the articulating arms 110-112 to move both vertically as well as in and out, in combination with the V-shaped fork of fingers 120 at the distal ends, is what gives the present system its adaptability, e.g., to completely withdraw the plunger to fully fill any of a variety of different oral syringe sizes.

Figure 13:
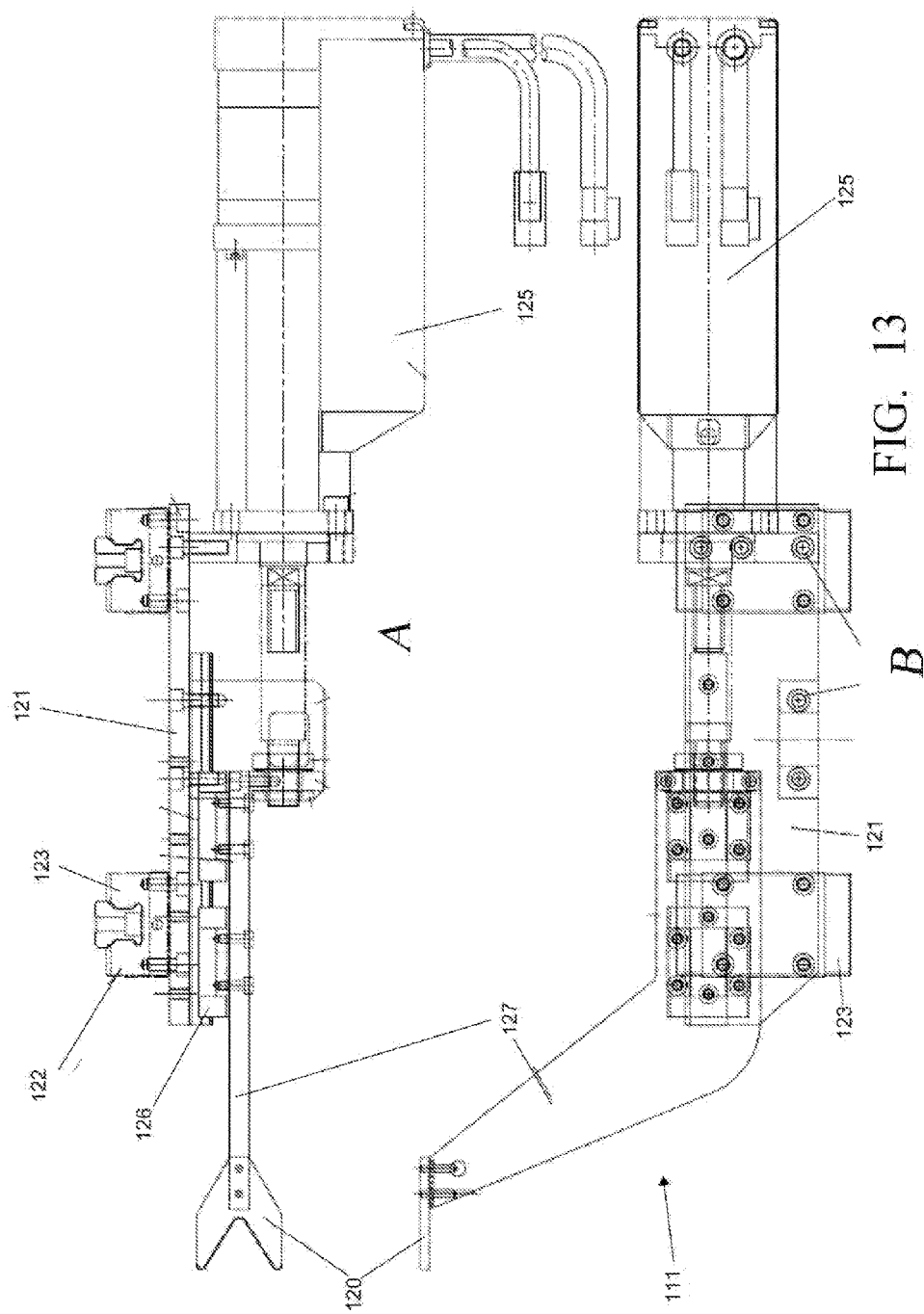
FIG. 13A is a top view and 13B a side view of an embodiment of the syringe gripping arms 111 and its drive mechanism.

The upper and middle arms 110, 111 grip above and below the syringe barrel flange, while the lower arm 112 grips the plunger flange. The local OSPS computer calculates the distance to move the lower arm 112 and plunger flange to extract the appropriate dose of medicine based on the prescribed dose volume V and known radius or diameter of the syringe S size retrieved. The linear travel distance H equals $V/\pi r^2$ where the radius r is stored in the database. The linear travel distance H constitutes the distance that the lower arm 112 needs to travel to pull the correct amount of medicine into the syringe S. The local OSPS computer then controls the movement of fill arms 110, 111, 112 in accordance with the calculated distance H, and may also account for other variables such as medicine viscosity, volume of fill, etc. to optimize either the linear travel distance H or the filling force exerted or filling time taken along that distance. Upper, middle and lower arms 110, 111 and 112, are provided in a single stacked configuration, along with a plunger lifting arm 128 that extends upward from below to depress the plunger of the inverted syringe S into the barrel. A seen in FIG. 13 each of the middle and lower arms 110, 111 and 112 have a horizontally fixed base member 121 riding on a pair of ball slides 122 on a set of guide rails 123 vertically oriented with the housing 895 (of FIG. 10). Vertical movement of each base member 121 on the guide rails 123 is controlled by a linear servomotor 124 situated below and extending into the housing 895. Each arm 110, 111, 112 is also provided with a horizontal reaching member 127 slideably mounted horizontally to each base member 121 so as to ride up or down the guide rails 123 with the base member 121 while being extendable or retractable in the horizontal to engage the syringe S. Horizontal extension and retraction of the reaching members 127 is controlled by a horizontally oriented linear servomotor 125 fixedly mounted to each base member 121 and engaged to the proximate reaching element 127, each which is itself mounted via a horizontally oriented ball slide assembly 126 affixed to the base member 121. The forked fingers 120 are horizontally disposed at the distal ends of the reaching elements 127. In this way the horizontal and vertical motion of each arm 110, 111, 112 is individually controllable in two dimensions.

Referring back to FIG. 10, in addition to the upper, middle and lower arms 110, 111, 112, a plunger lifting arm 128 extends upward from below to depress the plunger of the syringe S into the barrel as will be described. The plunger lifting arm 128 is controlled by a linear servomotor and is vertically oriented. In certain embodiments the lower arm 112 may serve both the plunger pull-down (withdraw) and plunger lift (depress) operations.

The container is automatically loaded into the syringe fill/cap station 5 at the product interface 81, as shown in FIG. 10. The interface comprises an offset yoke 82 that engages the adapter cap 210 between the upper and lower flanges 214, suspending the container 104. The operator signals "ready" by pressing a button at the control interface.

Once verified to be the correct, a fill arm 105 comprising a pair of grippers 143 are moved over the yoke 82 around the flanges capturing the container 104 in position. The grippers 143 are slideable toward and away from each other and are provided with a series of surface features such as grooves and ridges in their opposing faces to cooperatively engage those defined in the container adapter cap 210 to facilitate secure engagement with and gripping of the cap.

Movement of fill arm 105/gripper arms 143 over the yoke 82 may be accomplished by slideably mounting the fill arm 105 on an arm carriage 106, and mounting the arm carriage 106 in slots on a rotator arm 140. A actuator 142 is provided on bracket 143 with horizontal ball slide and track 141 mounted on or in the housing of the syringe fill/cap station 5 so as to be advanceable forward and backward between a syringe S in the staging area 81 and the filling position at the other end. Actuator 142 may be a linear actuator for sliding the bracket 143 on its track(s) 141 between the forward and back positions or to its home position between the two extremes. Pneumatic inlets are provided for opening/closing gripper jaws 143, and for flipping the container 104. Fixedly attached at a distal end of the rotator arm carriage 106 is the fill arm 105 including grippers 143 disposed to engage the adapter cap 210 of the container 104 when the container is situated in the product interface 81. The container rotator/inverter assembly may include a conventional servomotor 109 with perpendicular axis attached at the lower end of the rotator arm 140. This way, after capturing the container 104, the servomotor 109 flips the container 180 degrees forward, inverting it, and moving it into a fill position and orientation for filling of the syringe S. If the medicine in container 104 must be shaken, the servomotor 109 first shakes the container back and forth before flipping it.

During fill operations the upper, middle and lower arms 110, 111 and 112 are initially in a horizontally retracted state. When the syringe S is loaded, the upper and middle arms 110, 111 are extended so that the syringe is received within the V-notch and the fingers 120 are engaged to the surface of the barrel (upper arm 110) and plunger (middle arm 111) (see FIG. 10 inset and FIG. 12) such that the barrel flange is between the upper and middle arms. The upper and middle arms 110, 111 then slide vertically toward each other to tightly grip the barrel flange between them. The opposing surfaces of the upper and middle arms 110, 111 may be provided with a resilient and/or high friction surface to securely engage the barrel flange. The lower arm 112 engages the plunger above the plunger flange in a similar manner while the lift arm 128 extends upward to engage the distal end of the plunger. The lower and lift arms 112, 128 are brought together to engage trap the plunger flange between them.

The gripper 143 engages the adapter cap of the medicine container in the product interface 81 securely gripping the cap and engaging the container 104 between its fingers 143. The arm carriage is then advanced forward to withdraw the container 104 from the product from the inverted position B of interface 81. If needed, the rotator arm 108 is actuated in a back-and-forth motion to agitate or shake-up the medicine within the container 104. Once mixed (if necessary), the rotator arm 108 is rotated fully forward to invert the container over the syringe S such the adapter cap is aligned over the tip of the syringe. The syringe is then lifted by coordinated movement of the arms 110, 111, 112, 128 such that the nozzle is sealingly engaged within the elastomeric insert 225 of the adapter cap 210.

If the syringe S is entirely evacuated at this stage (i.e. the plunger is fully depressed within the barrel), the lower arm 112 is initially dropped, withdrawing the plunger from the barrel and drawing the medicine into the syringe. As noted, in certain embodiments the syringe may have a predetermined amount of air in the barrel to pre-pressurize the container 104. In such a situation the position of the plunger (and hence the volume of air in the barrel to be injected into the container) is determined by the system based on known parameters of the medicine, the container volume and its current fill level, and the plunger is positioned accordingly prior to insertion into the adapter cap by relative movement of the upper, middle, lower and lifting arms 110, 111, 112 and 128. Upon insertion of the tip in the adapter cap the plunger is first fully depressed by the lift arm 128 to pressurize the container and subsequently withdrawn by the lower arm 112 at a predetermined rate to fill the syringe S with desired amount of medicine without cavitation.

When the syringe is filled to the desired level, the arms 110, 111, 112 and 128 are lowered in unison and the syringe S is withdrawn from the adapter cap 210 and the elastomeric insert 225 returns to it closed/sealed position. If desired, the syringe plunger may be further withdrawn from the barrel slightly by relative movement of the lower arm 112 as the nozzle is withdrawn to draw in any medicine left in the elastomeric insert 225 so as to avoid drippage.

With the syringe withdrawn, the rotator arm 140 (FIG. 10) rotates to lift the container 104 into an upright position and the lower and lift arms 112, 128 disengage the plunger. The upper and middle arms 110, 111 return the syringe to the loading carriage 70.

The automated capper 147 may place a cap on the open tip of the filled syringe, fed from an inclined capping chute 149. Where capping is not automatic, the operator may manually place a cap over the tip prior to weighing.

Figure 14:
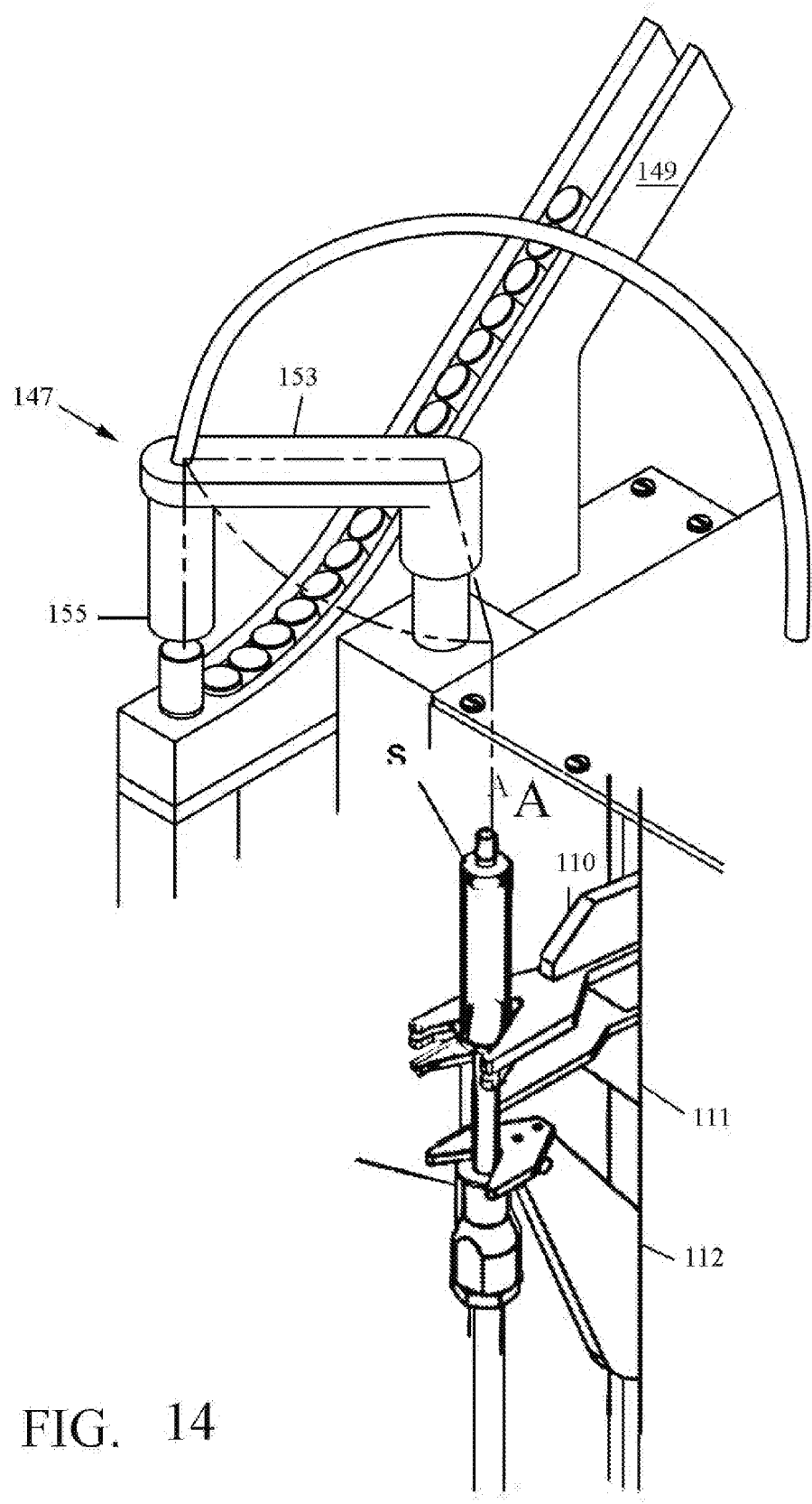
FIG. 14 is a perspective view of an exemplary automated capper 147 and inclined capping chute 149.

FIG. 14 illustrates the automated capper 147 and inclined capping chute 149. Automated capper 147 is a robotic capper under control of the Local OSPS computer with a servomotor-controlled positioning arm 153 and pneumatic capping mechanism with a distal cap-gripping chuck 155. The positioning arm 153 is positioned over caps fed from chute 149 and picks and places them on the inverted syringes while held in arms 110-112 in the loading position (A).

During batch operation a series of syringes S to be filled with the same medicine may be queued and loaded in sequence by the operator for filling. When no more syringes are to be filled with the particular medicine, the local container 104 is returned to the product interface 81 to be removed and returned under local OSPS Computer control to the medicine Storage facility 2.

After filling at the syringe fill/cap substation 5, the shuttle 52 moves along conveyor section A to and hands the filled/capped syringe S off to the handoff turret 57. Shuttle 52 returns to fill another syringe. The handoff turret 57 transfers the filled syringe to another shuttle 52 on conveyor section B, whereupon it continues through the remaining substations.

Referring back to FIG. 2, shuttle 52 carries the syringe to the inspection system 6 to cross check the weight and/or volume of the filled syringe against the expected weight/volume (the expected weight is based on the known weight of the empty syringe and the volume of the prescribed medicine). The vision inspection (FIG. 7) preferably entails an optical volume inspection based on the location of the syringe S plunger, the volume above the plunger and below the syringe tip. The filled and capped syringe S is preferably held stationary in a spring-loaded yoke holder by its cap, while the backlit camera CCD measures from a reference point to the seal ring of the syringe plunger. Since the syringes are hung by their caps within a common yoke they will all have the same zero reference point, despite varying sizes. Given knowledge of the prescribed dose and the syringe size, the system can accurate determine if the fill dose is correct. In addition, the vision inspection may also include phase-contrast imaging to measure bubbles in the syringe. Phase contrast imaging exploits differences in the refractive index of the contents to differentiate bubbles. Some bubbles are tolerable, but too many are not. The vision inspection may employ phase-contrast imaging as a bubble check. If the inspection station 6 determines that the syringe is filled to the correct volume and/or weight with an acceptable amount of bubbles, it will be accepted. Otherwise it will be rejected.

After inspection of filled syringe S as described above, the syringe is shuttled into a syringe label printer/applicator 9

(see FIG. 2). The labeler 9 is in communication with the central controller and prints and applies self-adhesive labels bearing information regarding the prescription such as the contents of the syringe (medicine, dosage, scheduled administration, etc.) and its intended recipient (name, room number, etc.) along with a bar code identifying a central record of this information. The label is printed, scanned (inspected) and, if approved, applied to the syringe using known application methods. In one such method the label is supported by the hinged arms of the applicator by vacuum pressure while the applicator advances to envelop the syringe barrel with the hinged arms coming together to join the label as a flag to the barrel. A portion of the label around the barrel must be transparent to permit dosage markings of the syringe to be clearly visible.

The labeled, filled and capped syringe is then bagged at bagger 7 for distribution to the patient, the bag itself being labeled with information similar to that found on the syringe label. Bagger 7 may be any suitable commercially-available bagger with a network-capable bag printer, bag storage/ dispenser, and heat seal assembly. A variety of automatic "tabletop bagger/printers" are available for this purpose.

Figure 15A:
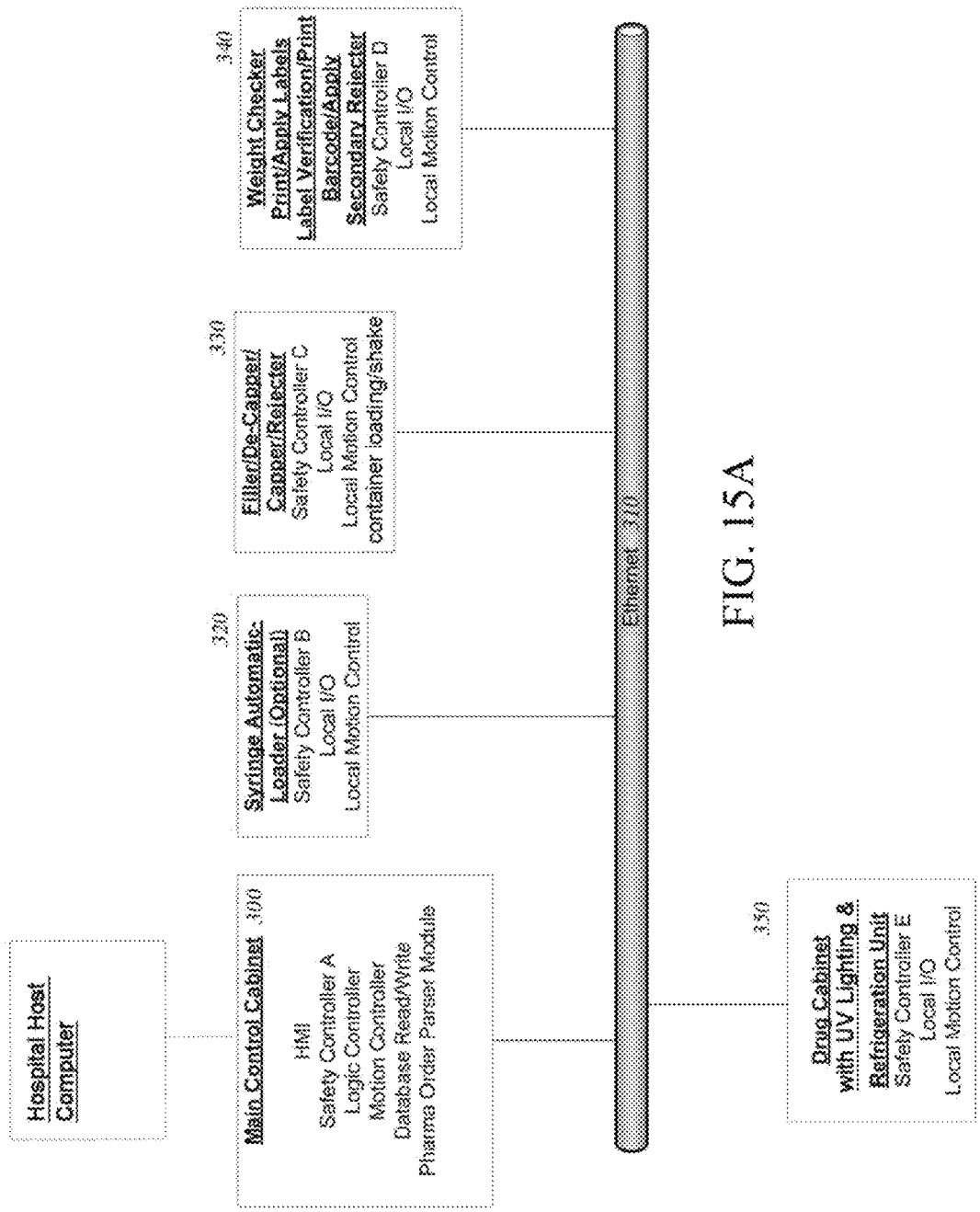
FIGS. 15A and 15B illustrate an exemplary control system architecture for the system 100 of FIGS. 2-12.
Figure 15B:
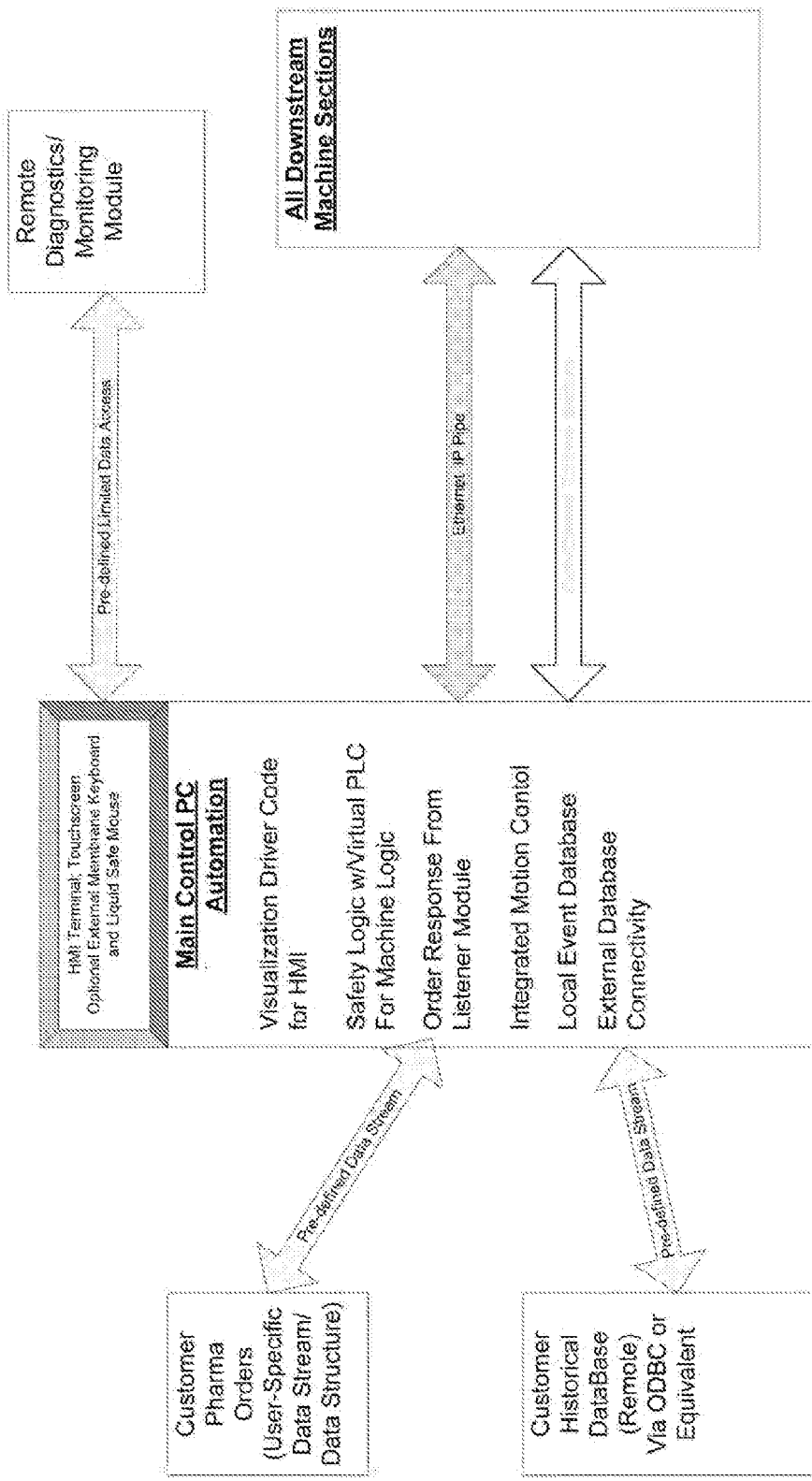

With reference to FIG. 15 a control system architecture (shown at (A) top) for the system 100 is disclosed in which a main controller 300 is provided in communication with a series of sub-controllers for one or more sub-station steps via a communications backbone 310, in the depicted case, via Ethernet. The main controller 300 is preferably a microprocessor based microcontroller or PC containing a processor core, memory, and programmable input/output peripherals. The controller contains a system safety controller, logic controller, top level motion controller and human-machine interface for interaction with a system operator. The main controller 300 further incorporates a database read/write module for interaction with a local or remote customer (patient) records database and local event database for managing downstream component operation. An order listener/parser module is provided for receiving orders from an external pharmacy/prescription entry and management system maintained by the institution. The parser can be custom formatted to discern and populate order information based on a user specified data stream and structure.

Sub-controllers are provided for all downstream machine sections such as a Syringe Auto-loader subcontroller 320 for the nozzle tip orienter 8, Filler/Capper/Rejecter 330, Checker/Verifier and Secondary Rejecter 340 and Medicine Library 350. The sub-controllers are each provided with a safety controller, local input/output system and local motion controller integrated with the main controller 300 via the communications backbone 310. The main controller orchestrates the integration and operation of the downstream machine elements as described above and controls the overall operational mode of the system 100.

The local OSPS Computer may incorporate fill weight/ volume adjustment software. Specifically, the inspection station 6 is networked to the Local OSPS Computer and may provide weight or volume feedback to automatically adjust the amount of liquid transferred into the oral syringe at servomotor-operated syringe fill/cap station 5. The software determines if a syringe has too much or too little medicine in it. Any out-of-specification syringe will be rejected and another one will be prepared utilizing feedback from the fill weight/volume adjustment software.

Figure 16:
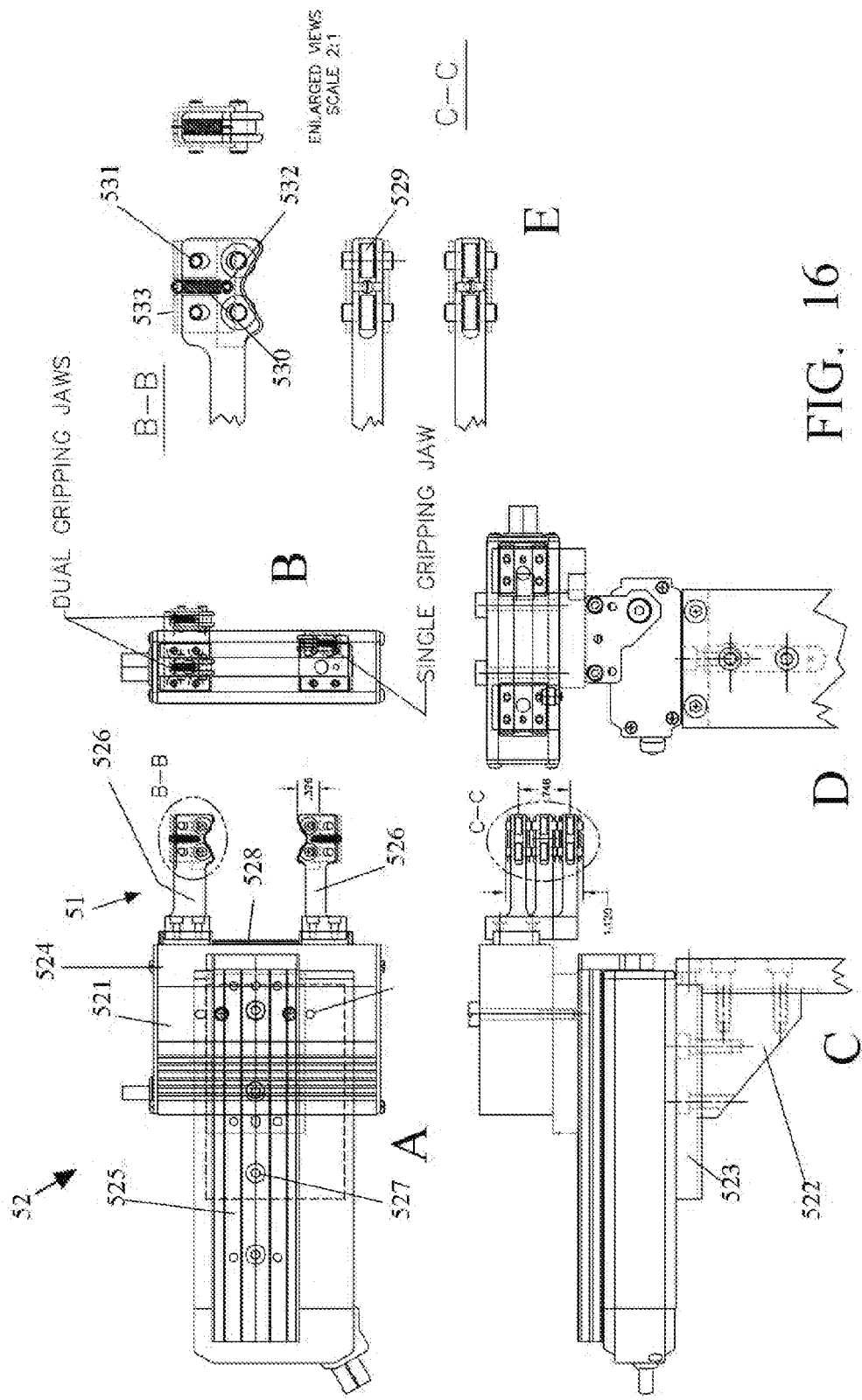
FIG. 16 is a composite view of a top (A), partial front (B), side (C) and full front view (D) if an exemplary shuttle gripper 52 of conveyor 50.

FIG. 16 is a composite view of a top (A), partial front (B), side (C) and full front view (D) if an exemplary shuttle gripper 52 of conveyor 50, with enlarged insets showing the gripper 51 details. Each gripper 52 generally comprises a servomotor 521 mounted on a rail 525 via set screws 527, the rail being mounted atop a shelf 523. Shelf 523 is in turn mounted on a pedestal 522 that travels along conveyor 50. Thus, servomotor 521 can be adjusted along rail 525 and repositioned via set screws 527 A gear box 524 is mounted to the face of the servomotor 521 for linearly-translating one or both of two opposed gripper arms 526 toward and away from each other, the movable gripper arm 526 being mounted in a tongue-and-groove track that spans the face of the gearbox 524. The gripper arms 526 protrude horizontally outward from the gripper 52 toward the various substations of system 100 for gripping and transporting medicine containers between them. Each gripper arm 526 is defined by an inwardly-disposed V-shaped jaw with recessed roller bearings 529 held captive in the gripper arm 526 and protruding slightly outward into the V-shaped recess of the jaw. The roller bearings 529 are damped by mounting them, e.g., on a floating plate 533 that is slidable within the gripper arm 526, plate 533 having a plurality of posts 531 protruding up into oblong slots in the gripper arm 526 to give plate 533 a limited range of travel. A spring 530 is stretched between anchors on the plate and gripper arm 533 to bias the plate 533 inward, hence increasing the protrusion of the roller bearings 529 into the V-shaped jaw. This way, as the roller bearings 529 compress against the body of a medicine container and/or syringe they damp the contact. Roller bearings 529 also allow rotation of the container/syringe held captive therein, which is important during orientation of the syringe nozzles. This configuration affords a firm but flexible grip on the annular container/syringe bodies. In the case of syringes S, the opposed V-shaped jaws are sized and spaced to accommodate any of the following standardized oral syringe sizes: 0.5 ml, 1 ml, 3 ml, 5 ml, 10 ml, 20 ml, 35 ml, and 60 ml. Importantly, when the grippers 52 retrieve a syringe S into its conforming V-shaped jaws of gripper arms 526, feedback from the servomotor 521 allows the local OSPS Computer to ascertain the syringe S size, thereby cross-checking to prevent the infeed of a wrong-sized syringe. This affords a reliable syringe infeed pick and place mechanism for shuttling syringes between substations.

The OSPS System 100 is specifically designed to dispense from a library 8 of up to 250-300 (or more) liquid medications into 0.5 ml, 1 ml, 3 ml, 5 ml, 10 ml, 20 ml, 35 ml, and 60 ml size syringes (both clear and amber) based on the doctor's prescription on a fully-automated basis. Its automated throughput is approximately 10-30 syringes per minute based on 1-10 ml size syringes, with inspection checks at each step in the process to ensure that the syringe was packaged correctly. The Track, Trace and Validation Software module documents the entire filling and packaging process and generates an audit trail available for recall in the future. It is important to understand that the preferred embodiment of the OSPS System 100 is designed for automatic operation, thereby avoiding all the typical human errors.

Figure 17:
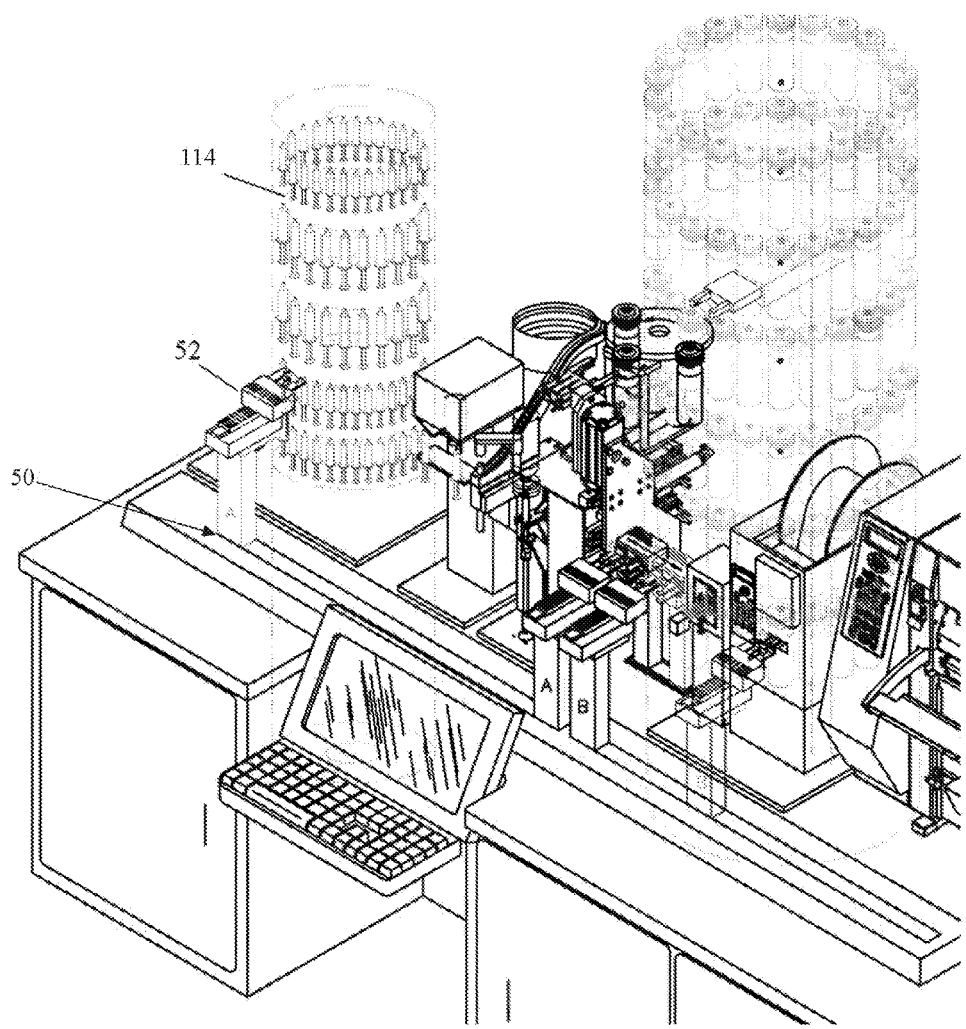
FIG. 17 is a perspective view of an alternate embodiment of the present system 100 in which the syringe storage 114 is a rotating multi-tiered servomotor-driven carousel rather than an inclined chute dispenser 113 as in FIG. 2.

FIG. 17 is a perspective view of an alternate embodiment of the present system 100 in which the syringe storage 114 is a rotating multi-tiered servomotor-driven carousel rather than an inclined chute dispenser 113 as in FIG. 2. This configuration may arrange the standardized oral syringe sizes: 0.5 ml, 1 ml, 3 ml, 5 ml, 10 ml, 20 ml, 35 ml, and 60 ml on a plurality or rotary tiers, and can make picking the appropriate syringe faster inasmuch as the servomotor-driven carousel 114 rotates simultaneously with linear movement of the shuttle 52 until its gripper 51 can retrieves the syringe from the proper magazine.

FIG. 18 is a perspective drawing of the sectionalized syringe conveyor 50 for shuttling along the Automated Filling/Packaging Station 4, adapted for use with the rotating multi-tiered servomotor-driven carousel 3 syringe storage of FIG. 17. The carousel dispenser 3 itself comprises a plurality of independently servo-rotated tiers, and the shuttle 52 is mounted atop a vertical positioner for vertical extension and up/down access to the respective tiers. As in FIG. 11, there are two independent sections "A" and "B" each bearing one movable shuttle 52, and a handoff turret 57 between sections. A shuttle 52 moves along conveyor section A to pick a syringe from syringe storage 3, move it into the nozzle tip orienter 8, and then into the syringe fill/cap station 5, after which it hands the filled/capped syringe S off to the handoff turret 57. The handoff turret 57 simply transfers the filled syringes for access by the shuttle gripper 51 of conveyor section "B", whereupon it continues through the remaining substations. Effective cycle time is approximately 19 seconds.

FIG. 18 also illustrates the use of a staging mechanism 117 in between the medicine container library 8 and the Automated Filling/Packaging Station 4 for staging a plurality of bulk medicine containers. The illustrated staging mechanism 117 is a starwheel indexer with a plurality of radially-spaced wells for staging medicine containers along a circular path. If several containers of a given medicine are needed to fulfill a batch of prescriptions or for any other reason this staging of multiple containers saves considerable time in the process.

FIG. 19 illustrates how the rotating multi-tiered servomotor-driven carousel 3 syringe storage of FIG. 17 and conveyor 50 can be doubled-up to increase throughput. The carousel 3 includes parallel-pairs of rows of syringes in each servo-rotated tier and two-side-by-side shuttles 52 move tandem pairs of syringes along independent sections "A" and "B" (each bearing a pair of movable shuttles 52), with a double handoff turret 57 between sections. Two shuttles 52 move along conveyor sections A to pick two syringes from syringe storage 3, move them into the nozzle tip orienter 8, and then into the syringe fill/cap station 5, after which they hand the filled/capped syringes S off to the handoff turret 57. The handoff turret 57 simply transfers the filled syringes for access by the shuttle gripper 51 of conveyor section "B", whereupon it continues through the remaining substations. Effective cycle time is approximately halved.

Figure 20:
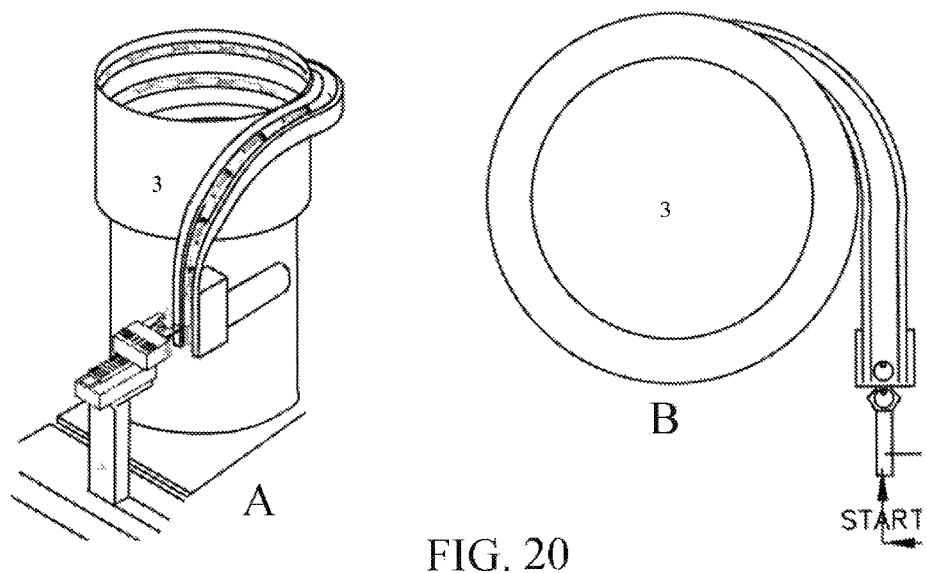
FIG. 20 is a composite perspective view of a vibratory syringe feeder bowl 3.

As still another alternative to the rotating multi-tiered servomotor-driven carousel, or inclined chute dispenser, a vibratory bowl feeder may be used as shown in FIG. 20. A variety of suitable vibratory bowl feeders are available for feeding individual syringes S, all include a bowl feeder that orients the parts, a vibrating drive unit upon which the bowl feeder is mounted, a control box module, and an outfeed track to convey parts along and discharge them to the gripper 52.

FIG. 21 is a perspective view of another alternate embodiment in which the linear syringe conveyor 50 is replaced by a pair of side-by-side rotary platforms 582 and all substations of the Automated Filling and Packaging Station 4 are arranged in a circle around the side-by-side rotary platforms 582. Each rotary platform 582 comprises a rotating base upon which is seated an axial array, for example, of six (6) extensible pistons each bearing a distal pair of gripper arms 526 (as per FIG. 16). The rotating multi-tiered servomotor-driven syringe storage carousel 3 is positioned at one end and the bagging station 7 at the other. In operation, the first rotary platform 582 retrieves a syringe from storage 2, rotates it around to the tip orienter 8, then to the fill/cap station 5, and then hands it off to the second rotary platform 582 for rotation around to the inspection station 6, syringe labeler 9, and bagging station 7.

Figure 22A:
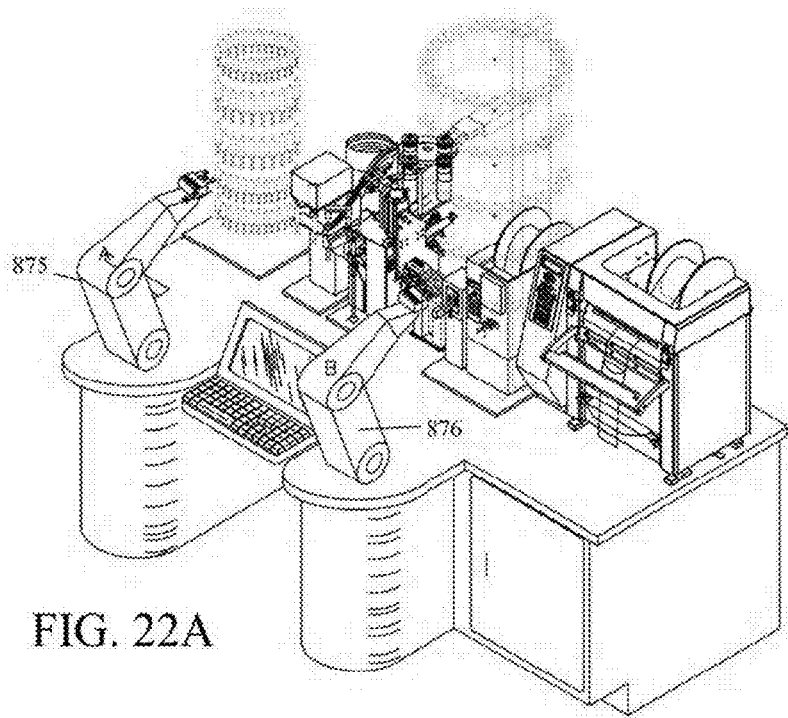
FIG. 22A is a perspective view and 22B a top view of another alternate embodiment in which the linear syringe conveyor 50 is replaced by robotic arms
Figure 22B:
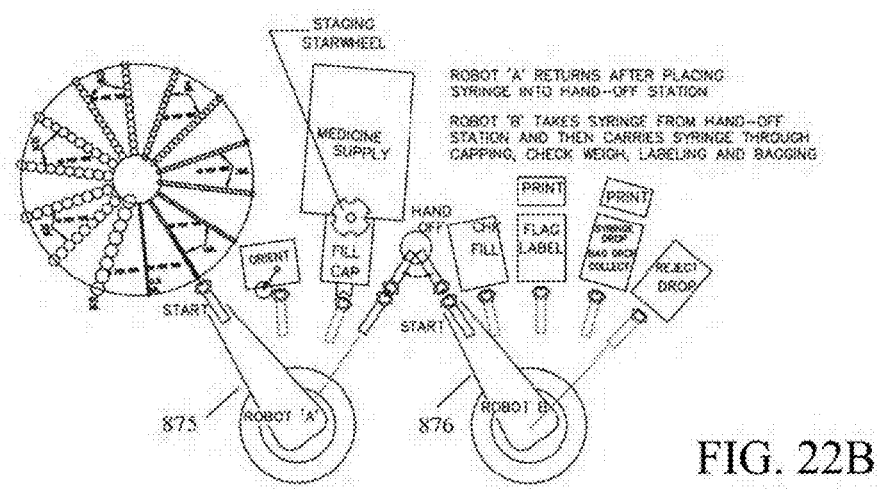

FIG. 22 is a perspective view of another alternate embodiment in which the linear syringe conveyor 50 is replaced by robotic arms networked to the local OSPS Computer for conveying syringes S and medicine containers 104 from station-to-station in place of the operator. If this is desired, then due to the extensive range required (approximately six feet) to traverse the distance of the current System 100, and the size of one robot, the inventors envision the use of two robot arms 875, 876. A first robotic arm 875 is responsible for syringe selection, orientation and filling/capping, while the second robotic arm 876 is responsible for inspection, syringe labeling and bagging. More specifically, the first robot arm 875 moves to select the proper syringe from syringe storage 3, and next holds the syringe S in place for orientation at orienter 6. Once oriented, arm 875 then moves syringe S into the fill/cap station 5, and then to inspection station 7. Once filled and inspected, a hand-off turret hands the syringe to the second robotic arm 876 for continuing on to the inspection station 6, syringe labeler 9, and bagging station 7.

Figure 23:
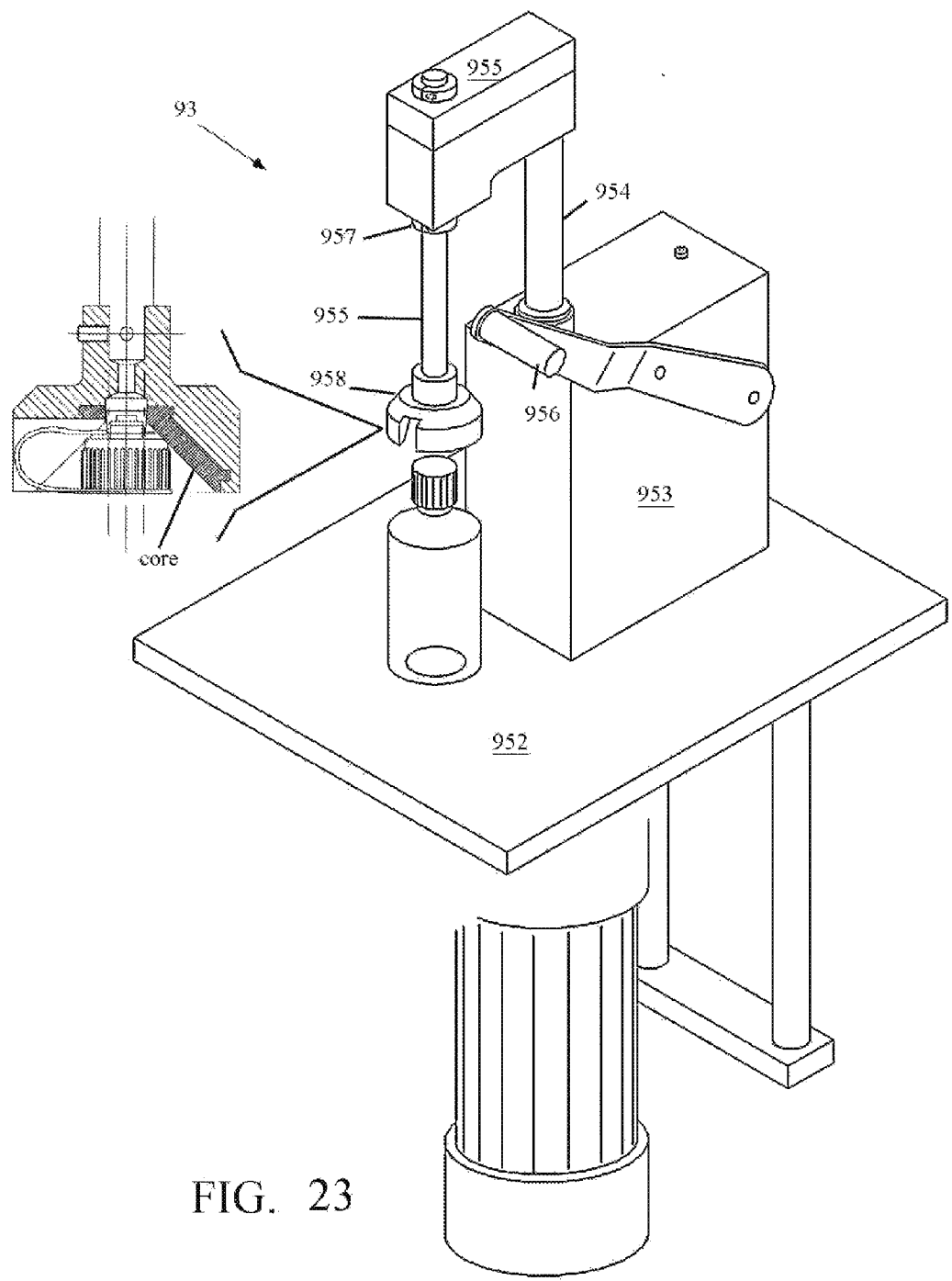
FIG. 23 is a perspective view of an exemplary capping/decapping station 93.

FIG. 23 is a perspective view of an exemplary capping/decapping station 93, which comprises an elevated platform support surface 952 for stabilizing the medicine container. An optional container clamp (not shown) may be mounted on the support surface 952 for centering and constraining the medicine container. The container clamp may comprises a pair of opposing V-shaped clamps. An operator presses a "clamp" button and the opposing V-shaped clamps close around the container bottle. The V-shaped clamps may be mounted on low-friction slides so that any size bottle can be slid toward the center of the chuck. Although the clamps are mounted on low friction slides, they remains stationary to rotation. An articulating spindle assembly extends upward from a base 953 mounted on the support surface 952, the spindle assembly including a vertical piston 954 extendable/retractable from base 953 and a horizontal mast 955 extending from piston 954. The mast 955 contains a motor which drives a vertical spindle 955. A manual lowering arm 956 is geared to the piston 954 for piston extension/retraction from base 953, thereby allowing an operator to raise or lower spindle 955 manually. A pressure sensor 957 is mounted to the spindle 955 (or internal to the mast 955 for sensing the downward pressure. A chuck 958 is mounted at the lower end of the spindle 955. As seen in the inset (at left), the chuck 958 is preferably formed with a hard outer shell (e.g., stainless steel) and a molded plastic core placed inside, the core defined by a conical interior surface with an elastomeric inner lining. An elastomer such as polyurethane or equivalent resin can be poured around the interior of the core to form the elastomeric lining. A lateral slot enters the interior of the chuck 958. This chuck 958 is designed to fit all caps ranging from 18 mm to 38 mm in diameter. Due to its conical interior and elastomeric inner lining, downward pressure onto the container cap causes a non-slip, gripping action. The slot accommodates certain container caps which have a tethered closure feature. The tether is free to protrude and will not cause interference between the chuck 958 and cap.

This capping/decapping station 93 enables the medicine caps to be loosened from their containers mechanically without the need for an operator to exert strong hand pressure. The system is capable of loosening caps as well as applying torque to seat them. In operation, the medicine container is placed on the support surface 952, and the operator centers the container either with the optional holding clamp or by hand, and if to cap a pre-labeled adapter cap is placed on the container. Upon moving the manual lowering arm 956 forward, the piston 954 extends from base 953, thereby a lowering spindle 955. The chuck 958 descends into contact with the adapter cap to tighten it, or into contact with the manufacturer cap if decapping is desired. Once the chuck 958 descends onto the cap and downward force is applied the pressure sensor 957 begins to compress and in doing so, signals the motor to start. This avoids inadvertent rotation of the elastomeric chuck 958 in advance of contacting the cap which may cause abrasion and emit particles of the elastomer in the vicinity of the work area. The scanner 95A (FIG. 2 may be mounted beneath the platform support 952 to reads the medicine container's 2D barcode from beneath. Preferably, the scanner 95A is synchronized via the OSPS computer such that the first time it reads a particular barcode the spindle 955/motor turn in the counter-clockwise (cap removal) direction. Conversely, the second time scanner 95A reads that particular barcode the spindle 955/motor turn in the clockwise (cap tightening) direction. The assembled medicine container and adapter cap can be slid out and removed.

Figure 24:
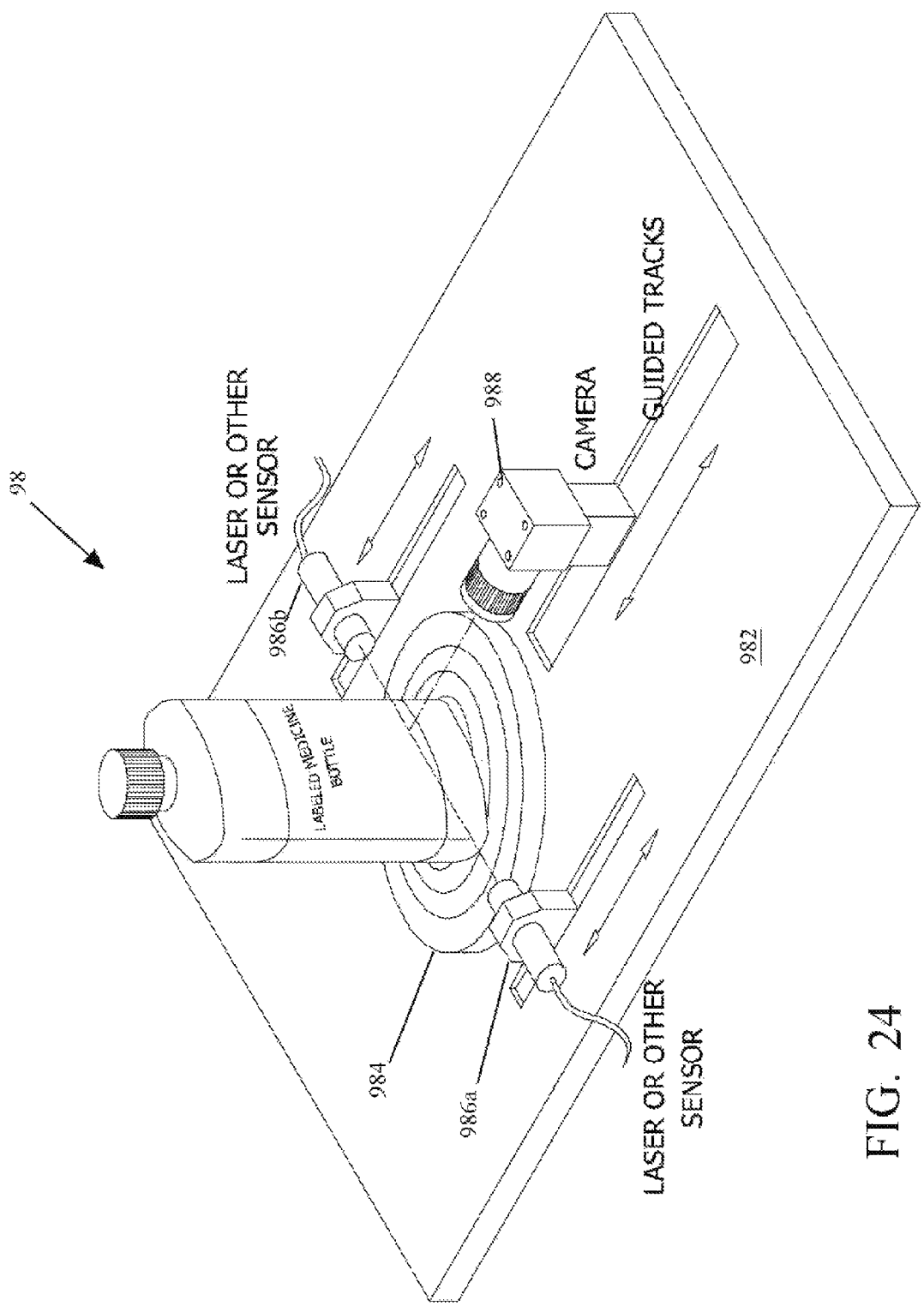
FIG. 24 is a perspective view of the label photographing station 98 resident at the Medication Container Orientation and Log-In Station.

FIG. 24 is a perspective view of the label photographing station 98 resident at the Medication Container Orientation and Log-In Station. The label photographing station 98 is employed for the purpose of photographing the entire medicine container's label for archival purposes (to retain a record of the medication used to fill a specific prescription). In some cases, the barcode scan from scanner 95A alone will be insufficient to identify details such as medicine concentration, expiration, handling and other precautions relative to the medication. The label photographing station 98 comprises a circular table 984 rotatably seated atop a support surface 982. A camera 988 is oriented directly toward a focal point centrally atop the table 984, and a pair of opposing sensors 986a, 986b are indirectly aimed from the sides toward that same focal point. The camera 988 and sensors 986a, 986b are all mounted on a common undercarriage via struts that pass through tracks in the table 984. This allows the camera 988 and sensors 986a, 986b to translate in unison along the tracks in the table 984. The undercarriage is servo-driven (or otherwise adapted for controlled translation) under control on the OSPS Computer, in accordance with feedback from sensors 986a, 986b. The medicine container may be manually placed anywhere atop the table 984, and the OSPS Computer will drive the undercarriage until the sensors 986a, 986b align with the surface of the medicine container. The sensors 986a, 986b track the surface of the container and travel with that focal surface, along with the camera 988. This positions the camera 988 at exactly the proper focal distance regardless of container position, and maintains the optimum focal distance from label to camera 988 despite a variety of sizes and shapes of medicine containers.

Figure 25:
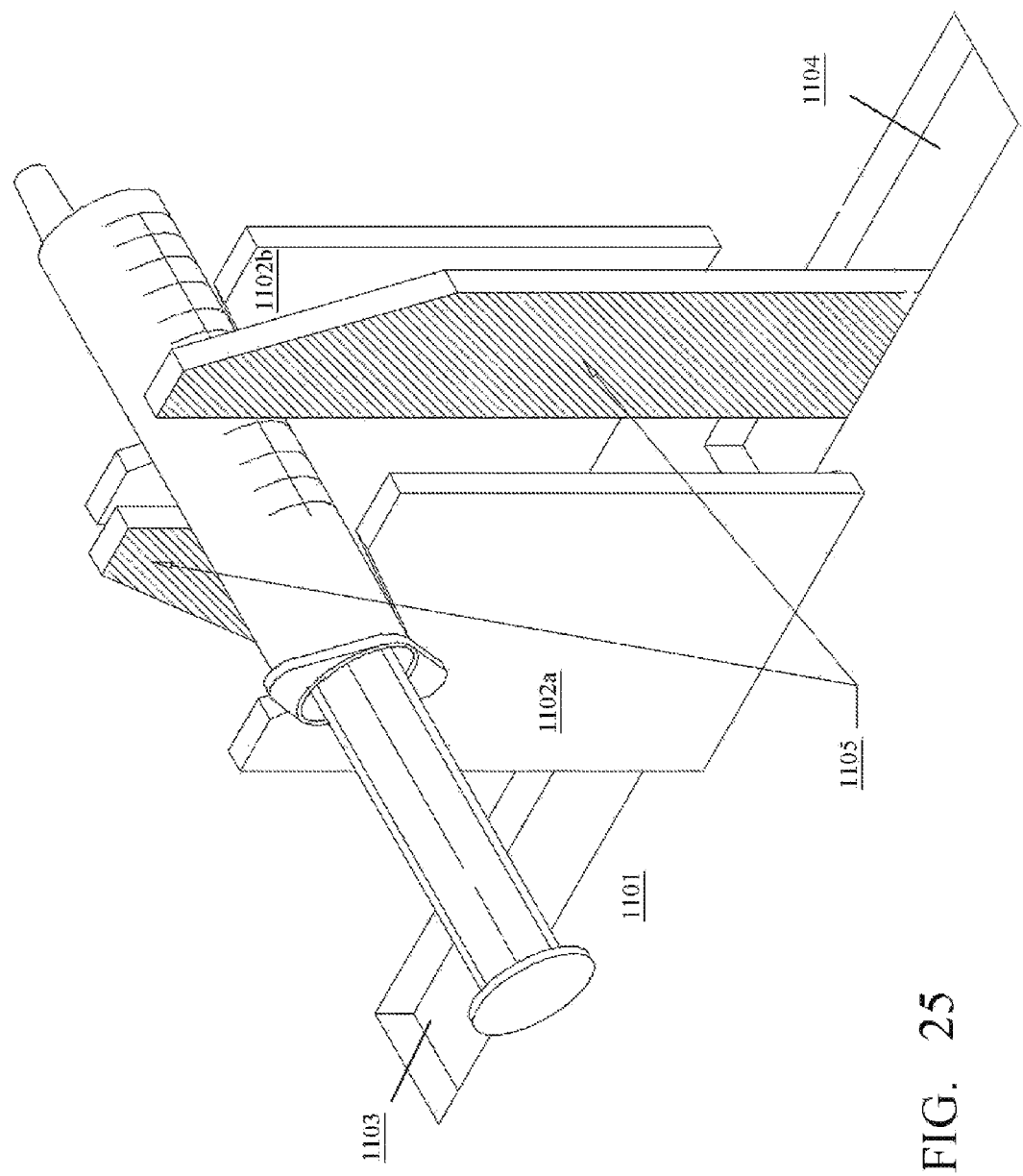
FIG. 25 is a perspective view of the syringe size inspection station 11 which verifies that the correct syringe has been selected.

FIG. 25 is a perspective view of the syringe-selection verification station 11 which verifies that the correct syringe size (0.5 ml, 1 ml, 3 ml, 5 ml, 10 ml, 20 ml, 35 ml, and 60 ml)) has been retrieved by the shuttle 52 and gripper 51 from the proper magazine. One skilled in the art should understand that syringe-selection verification station 11 may be placed anywhere along shuttle 52 between the filling/capping station and the syringe label printer and labeler substation 9. The illustrated syringe-selection verification station 11 essentially comprises a set of automatic calipers connected to the OSPS Computer for verifying proper syringe size. More specifically, a support surface 1101 is formed with a pair of aligned slots 1103, 1104. A stationary cradle comprises a pair of spaced-apart yokes 1102a, 1102b fixedly mounted on the support surface 1101 on opposite sides of the slots 1103, 1104 for supporting the syringe S in a horizontal position. A pair of articulating caliper fingers 1105 protrude upward through the slots 1103, 1104 to embrace the syringe S on both sides. Caliper fingers 1105 are driven by an underlying caliper drive mechanism connected to the OSPS Computer which moves fingers 1105 into contact with the syringe S after the shuttle 5s has deposited the syringe S onto the yokes 1102a, 1102b. The caliper fingers 1105 rise to a height higher than the center of the largest syringe S size, and in operation the fingers 1105 close around the body of the syringe S until a force is sensed (indicating contact with the syringe). At this point a measurement of the syringe body is taken (the distance between fingers 1105 is calculated) to verify that the correct syringe S has been selected. If correct, labeling and/or further processing of the syringe S will take place.

In addition to syringe S size, it may also be desirable to verify that proper syringe S color has been retrieved by the shuttle 52 and gripper 51 from the proper magazine. This entails a more comprehensive visual inspection, more than the digital caliper-type syringe-selection verification station 11 described above. Nevertheless, both color and size can be verified by optical imaging using hardware equivalent to the vision inspection station 6 used herein for verifying syringe fill volume.

The foregoing OSPS system 100 fulfills prescription orders in a just-in-time environment, and solves the problems inherent in the handling of all the myriad sized medication containers containing the pharmaceuticals to be dispensed, as well as variously-sized oral syringes, bringing them together in a controlled environment to quickly and accurately fill and label each syringe and to verify its work as it proceeds in order to avoid medication errors in the process. In other cases where a lesser degree of automation is preferred this is possible with a simplified filling system in which both syringes and medicine containers are manually selected, and mounted, and only the filling process is semi-automated. Still, track and trace may be applied for the purpose of ensuring that the correct medicine is selected.

In all the above-described embodiments, the system minimizes downtime as well as processing time to take and fill orders, and is easy to clean and capable of maintaining an environment free from cross contamination. The system is open and accessible and allows interaction and oversight by a human operator at multiple points in the operation. Moreover, it is modular and permits a differing and upgradeable level of operator participation (from manual/semi-automatic to and including full automation) based on the need of the individual institution.

It should now be apparent that the above-described system is driven by prescription orders in a just-in-time environment, manages all the various prescription containers containing the pharmaceuticals to be dispensed, as well as variously-sized oral syringes, to automatically converge them and orient, fill, label and cap each syringe and fully verify its work as it proceeds in order to avoid medication errors in the process. The pharmacy automation system for oral syringes substantially improves the pharmacist and technician productivity, maintains an environment free from cross contamination, minimizes operator fatigue, and minimizes prescription errors.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims and may be used with a variety of materials and components. This application is therefore intended to cover any variations, uses, or adaptations of the invention using its general principles. Further, this application is intended to cover such departures from the present disclosure as come within known or customary practice in the art to which this invention pertains.

We claim:

1. A system for automated filling of syringes with medicines from containers, said syringes being of various sizes and types all having a barrel, an annular flange encircling said barrel, a plunger slideably engaged in said barrel, and a flange at distal end of said plunger, the system comprising:
a programmable controller programmed with control software comprising computer instructions stored on non-transitory computer memory for determining a syringe size to fill a prescription, for guiding retrieval of a selected bulk medicine container to fill said prescription, for guiding retrieval of a selected syringe, and for controlling automatic filling of said selected syringe with medicine from said container, and an automated filling station in data communication with said programmable controller for automatically filling said selected syringe with medicine from said selected container of medicine, said system for automated filling of syringes further comprising a plurality of arms for manipulating said selected syringe, said plurality of arms terminating in a forked end for engaging said selected syringe, and each arm being independently controlled and articulating along two axes, thereby moving vertically and horizontally to withdraw a plunger of said syringe to fill said syringe with medicine.

2. The system for automated filling of syringes according to claim 1, wherein said plurality of arms includes at least a first arm and second arm.

3. The system for automated filling of syringes according to claim 1, further comprising a syringe storage assembly for storing a plurality of syringes of various sizes and types.

4. The system for automated filling of syringes according to claim 3, further comprising a first conveyor in communication with said programmable controller for conveying said selected syringe from said syringe storage assembly to said automated filling station.

5. The system for automated filling of syringes according to claim 4, further comprising a first syringe inspection station for verifying that a correct syringe has been selected.

6. The system for automated filling of syringes according to claim 5, wherein said first syringe inspection station verifies that a correct syringe size and color has been selected.

7. The system for automated filling of syringes according to claim 5, wherein said first syringe inspection station comprises an electronic caliper.

8. The system for automated filling of syringes according to claim 4, wherein said automated filling station includes a syringe loading assembly for indexing said selected syringe from said first conveyor to said automated filling station.

9. The system for automated filling of syringes according to claim 1, further comprising a bulk medicine container storage assembly.

10. The system for automated filling of syringes according to claim 9, further comprising a second conveyor in communication with said programmable controller for conveying said selected bulk medicine container from said bulk medicine container storage assembly to said automated filling station.

11. The system for automated filling of syringes according to claim 10, wherein said second conveyor includes a staging mechanism for staging a plurality of bulk medicine containers for use in filling syringes at said automated filling station.

12. The system for automated filling of syringes according to claim 10, wherein said selected bulk medicine container comprises a container equipped with an adapter cap having an annular body defined by an aperture through said body, and a valve covering said aperture.

13. The system for automated filling of syringes according to claim 12, wherein said adapter cap has at least one protruding flange for manipulation by said second conveyor.

14. The system for automated filling of syringes according to claim 12, further comprising a medicine container login station for applying said adapter cap onto one of said containers of medicine.

15. The system for automated filling of syringes according to claim 4, wherein said automated filling station includes a syringe loading assembly for indexing said selected syringe from said first conveyor to a filling position.

16. The system for automated filling of syringes according to claim 1, further comprising a bagging substation for bagging said filled syringe and for marking the bag.

17. The system for automated filling of syringes according to claim 1, further comprising a syringe fill-inspection station in communication with said controller for determining that said selected syringe filled with medicine at said automated filling station has been properly filled.

18. The system for automated filling of syringes according to claim 17, wherein said inspection substation optically determines a fill volume of said selected syringe with reference to a plunger position of said selected syringe.

19. The system for automated filling of syringes according to claim 18, wherein said inspection substation determines the presence of excess bubbles in said selected syringe by phase-contrast imaging.

20. The system for automated filling of syringes according to claim 1, further comprising a first labeler in communication with said controller for printing a scannable label for attachment to each selected syringe filled with medicine at said automated filling station.

21. The system for automated filling of syringes according to claim 20, further comprising a first scanner in communication with said controller for scanning a bar code attached to said selected syringe, adapter cap, or medicine container.

22. The system for automated filling of syringes according to claim 3, wherein said syringe storage comprises a syringe storage bin for retaining a plurality of syringes of different sizes, said storage bin comprising a plurality of compartments each for retaining a plurality of syringes of uniform size.

23. The system for automated filling of syringes according to claim 14, wherein said medicine container login station comprises a second labeler in communication with said controller for printing a scannable label for attachment to one or both of said medicine container and adapter cap.

24. The system for automated filling of syringes according to claim 23, wherein said medicine container login station further comprises a second barcode scanner in communication with said programmable controller for scanning the scannable label attached to the medicine container and/or adapter cap.

25. The system for automated filling of syringes according to claim 14, wherein said medicine container login station comprises a fixed focal length camera in communication with said programmable controller for photographing said medicine container.

26. The system for automated filling of syringes according to claim 25, wherein said camera is mounted on an articulating platform relative to said medicine container, said medicine container login station further comprising at least one sensor in communication with said programmable controller for sensing a position of said medicine container, whereby said programmable controller adjusts said articulating platform.

27. The system for automated filling of syringes according to claim 1, wherein said plurality of arms for manipulating said selected syringe includes at least a first arm, second arm and third arm, all of said arms being independently servo-controlled.

28. The system for automated filling of syringes according to claim 27, wherein said plurality of arms comprise distal V-shaped fingers.

29. The system for automated filling of syringes according to claim 1, further comprising an automated capping mechanism for capping filled syringes.

30. The system for automated filling of syringes according to claim 1, wherein said control software calculates an optimal syringe size for each prescription.

31. The system for automated filling of syringes according to claim 30, wherein said control software automatically determines when a bulk medicine container in said bulk medicine container storage does not contain enough medicine to fill said prescription.

32. The system for automated filling of syringes according to claim 30, wherein said control software automatically determines when a bulk medicine container in said bulk medicine container is past a predetermined expiration date.

33. The system for automated filling of syringes according to claim 4, wherein said first conveyor comprises a shuttle moving along a track.

34. The system for automated filling of syringes according to claim 33, wherein said shuttle comprises a pair of gripper arms.

35. The system for automated filling of syringes according to claim 34, wherein each gripper arm comprises a pair of rollers for allowing rotation of syringes carried therein.

* * * * *